United States Patent
Moreno et al.

(10) Patent No.: US 12,400,747 B2
(45) Date of Patent: Aug. 26, 2025

(54) SENSOR DRIVEN SECURE DISPENSING UNIT

(71) Applicant: Omnicell, Inc., Mountain View, CA (US)

(72) Inventors: Gerardo Moreno, Pleasanton, CA (US); John Foot, Monterey, CA (US); Edith Wilson, Healdsburg, CA (US); Vikram Mehta, Dublin, CA (US); Herbert Lawson Fisher, Portola Valley, CA (US)

(73) Assignee: Omnicell, Inc., Cranberry Township, PA (US)

(*) Notice: Subject to any disclaimer, the term of this patent is extended or adjusted under 35 U.S.C. 154(b) by 0 days.

(21) Appl. No.: 18/490,464

(22) Filed: Oct. 19, 2023

(65) Prior Publication Data
US 2024/0233902 A1 Jul. 11, 2024

Related U.S. Application Data

(63) Continuation of application No. 18/166,051, filed on Feb. 8, 2023, now Pat. No. 11,831,913, which is a
(Continued)

(51) Int. Cl.
*G16H 20/13* (2018.01)
*A61G 12/00* (2006.01)
(Continued)

(52) U.S. Cl.
CPC ......... *G16H 20/13* (2018.01); *A61G 12/001* (2013.01); *G16H 10/60* (2018.01); *G16H 40/20* (2018.01);
(Continued)

(58) Field of Classification Search
CPC ........ G16H 20/13; G16H 40/20; G16H 10/60; A61G 12/001
(Continued)

(56) References Cited

U.S. PATENT DOCUMENTS 5,562,232 A 10/1996 Pearson
5,927,540 A * 7/1999 Godlewski .......... G07F 17/0092
221/103
(Continued)

FOREIGN PATENT DOCUMENTS

AU 2021246647 A1 9/2022
CA 3101802 A1 12/2019
(Continued)

OTHER PUBLICATIONS

U.S. Appl. No. 16/834,950, Non-Final Office Action, Mailed On May 25, 2022, 8 pages.
(Continued)

*Primary Examiner* — Ahshik Kim
(74) *Attorney, Agent, or Firm* — Kilpatrick Townsend & Stockton LLP; Darin J. Gibby; Torrey D. Spink

(57) ABSTRACT

A secure dispensing unit includes a housing comprising a first end and a second end and a number of storage assemblies. The number of storage assemblies are arranged in parallel with one another within the housing. Each storage assembly includes a number of compartments arranged linearly along an axis of the housing with each of the compartments being configured to store an item. A cover is coupled with the housing and extends between the first end and the second end such that the cover is positioned over the compartments. An actuator is coupled with the cover, the actuator being configured to retract the cover to draw a distal end of the cover from the first end toward the second end to expose a selected number of compartments.

15 Claims, 17 Drawing Sheets

Related U.S. Application Data continuation of application No. 16/834,950, filed on Mar. 30, 2020, now Pat. No. 11,615,875.

(51) Int. Cl.

| | |
|---|---|
| *G16H 10/60* | (2018.01) |
| *G16H 40/20* | (2018.01) |
| *H04N 19/11* | (2014.01) |
| *H04N 19/117* | (2014.01) |
| *H04N 19/122* | (2014.01) |
| *H04N 19/124* | (2014.01) |
| *H04N 19/129* | (2014.01) |
| *H04N 19/13* | (2014.01) |
| *H04N 19/159* | (2014.01) |
| *H04N 19/174* | (2014.01) |
| *H04N 19/176* | (2014.01) |
| *H04N 19/426* | (2014.01) |
| *H04N 19/44* | (2014.01) |
| *H04N 19/463* | (2014.01) |
| *H04N 19/593* | (2014.01) |
| *H04N 19/61* | (2014.01) |
| *H04N 19/625* | (2014.01) |
| *H04N 19/82* | (2014.01) |
| *H04N 19/96* | (2014.01) |

(52) U.S. Cl.
CPC ........... *H04N 19/11* (2014.11); *H04N 19/117* (2014.11); *H04N 19/122* (2014.11); *H04N 19/124* (2014.11); *H04N 19/129* (2014.11); *H04N 19/13* (2014.11); *H04N 19/159* (2014.11); *H04N 19/174* (2014.11); *H04N 19/176* (2014.11); *H04N 19/426* (2014.11); *H04N 19/44* (2014.11); *H04N 19/463* (2014.11); *H04N 19/593* (2014.11); *H04N 19/61* (2014.11); *H04N 19/625* (2014.11); *H04N 19/82* (2014.11); *H04N 19/96* (2014.11)

(58) Field of Classification Search
USPC .................................................... 375/240.12
See application file for complete search history.

(56) References Cited

U.S. PATENT DOCUMENTS

| | | | |
|---|---|---|---|
| 6,338,007 | B1 | 1/2002 | Broadfield et al. |
| 8,195,328 | B2 | 6/2012 | Mallett et al. |
| 8,972,051 | B2 | 3/2015 | Rahilly et al. |
| 11,615,875 | B2 | 3/2023 | Moreno et al. |
| 11,831,913 | B2 | 11/2023 | Moreno et al. |
| 2011/0196538 | A1 | 8/2011 | Michael |
| 2013/0070090 | A1 | 3/2013 | Bufalini et al. |
| 2015/0305500 | A1* | 10/2015 | Biba .................. A47B 88/57 312/330.1 |
| 2016/0324314 | A1 | 11/2016 | Duval et al. |
| 2017/0018136 | A1 | 1/2017 | McFarland |
| 2017/0109480 | A1 | 4/2017 | Vahlberg |
| 2019/0214123 | A1 | 7/2019 | Parviainen |
| 2019/0390482 | A1 | 12/2019 | Rahilly |
| 2021/0304122 | A1* | 9/2021 | Dattamajumdar ..... G16H 40/20 |
| 2021/0304862 | A1 | 9/2021 | Moreno et al. |

FOREIGN PATENT DOCUMENTS

| | | |
|---|---|---|
| CN | 115426923 A | 12/2022 |
| EP | 4125499 A1 | 2/2023 |
| KR | 20220159419 A | 12/2022 |
| WO | 2021202112 A1 | 10/2021 |

OTHER PUBLICATIONS

U.S. Appl. No. 16/834,950, Notice of Allowance, Mailed On Nov. 2, 2022, 8 pages.
U.S. Appl. No. 18/166,051, Notice of Allowance, Mailed On Jul. 21, 2023, 8 pages.
Application No. CN202180026236.0, Office Action, Mailed On Dec. 8, 2024, 9 pages.
Application No. EP21780165.3, Extended European Search Report, Mailed On Dec. 19, 2023, 9 pages.
EP21780165.3, "Intention to Grant", Oct. 24, 2024, 9 pages.
Application No. PCT/US2021/022955, International Preliminary Report on Patentability, Mailed On Oct. 13, 2022, 10 pages.
Application No. PCT/US2021/022955, International Search Report and Written Opinion, Mailed On Jun. 8, 2021, 11 pages.

* cited by examiner

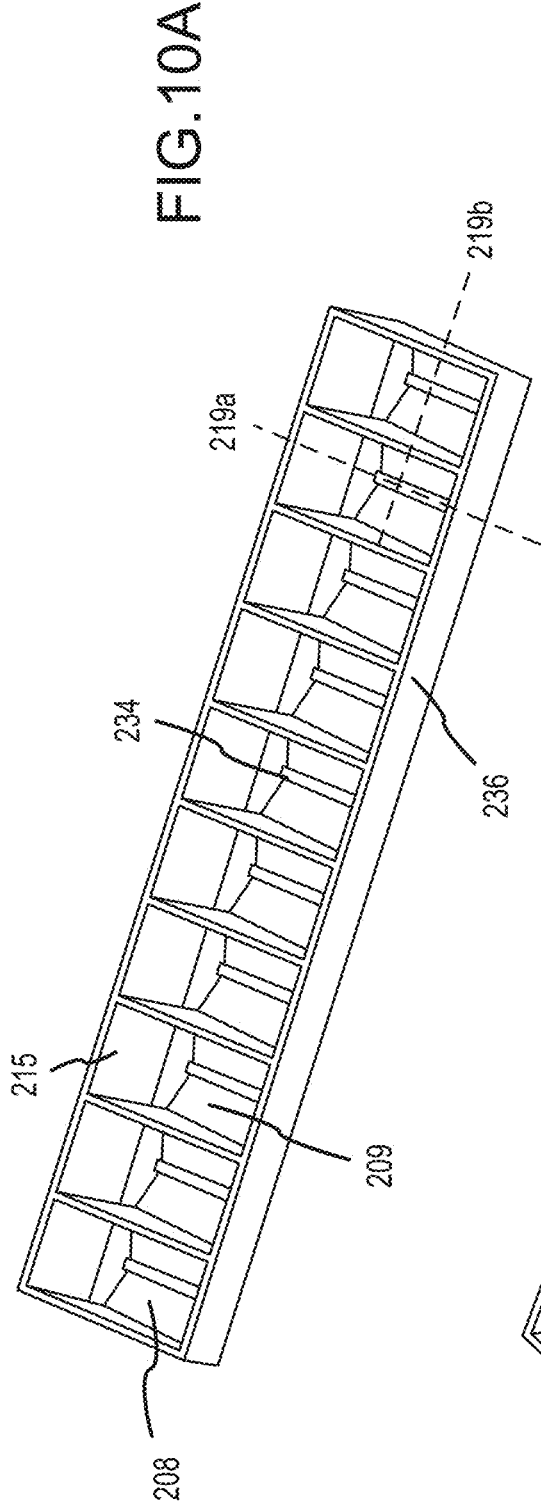
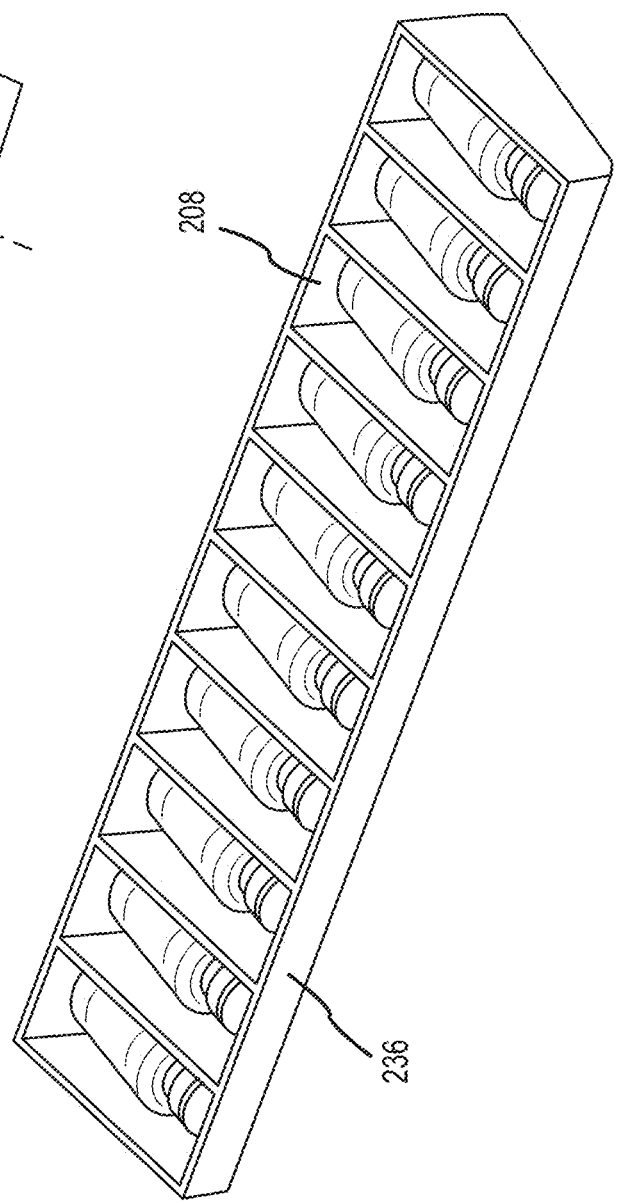

SENSOR DRIVEN SECURE DISPENSING UNIT

CROSS REFERENCE TO RELATED APPLICATIONS

This application a continuation of U.S. patent application Ser. No. 18/166,051, filed Feb. 8, 2023, which is a continuation of U.S. patent application Ser. No. 16/834,950, filed Mar. 30, 2020, the complete disclosure of which is hereby incorporated by reference for all intents and purposes.

BACKGROUND OF THE INVENTION

Many industries rely on the accurate inventory and dispensing of secure items. For example, in a hospital setting, it is of paramount importance that patients be given the correct medications in the correct doses. In addition, it is legally required that controlled substances be securely stored and tracked to maintain proper levels of inventory and also to determine proper consumption. It is also important that inventories of medications and supplies be tracked so that proper business controls can be implemented.

Various dispensing cabinets and carts have been developed to assist in the management of medications and other items. However, improvements are still desired in the reliability of dispensing and tracking of items, and it is also desirable to reduce the amount of space required for item storage and dispensing.

BRIEF SUMMARY OF THE INVENTION

Embodiments of the present disclosure are directed to systems and methods for providing selectable controlled access to items stored within secured compartments. Embodiments may include a retractable cover that provides access to only the number of items selected by a particular user, without exposing any additional items or compartments. Additionally, embodiments of the present invention may help maintain inventory counts by keeping track of the actual presence of items, not just what the users say they are taking. This allows accurate inventory counts to be maintained in the event of user error and/or fraudulent behavior.

In one embodiment, a dispensing unit is provided. The dispensing unit may include a housing comprising a first end and a second end and a number of storage assemblies. The number of storage assemblies may be arranged in parallel with one another within the housing. Each storage assembly may include a number of compartments arranged linearly along an axis of the housing with each of the compartments being configured to store an item. The storage assembly may include a cover coupled with the housing and extending between the first end and the second end such that the cover is positioned over the compartments to secure items held therein. The storage assembly may further include an actuator coupled with the cover. The actuator may be configured to retract the cover to draw a distal end of the cover from the first end toward the second end to expose a selected number of the plurality of compartments.

In another embodiment, a dispensing unit may include a housing comprising a first end and a second end and a number of compartments arranged linearly along an axis of the housing, with each of the compartments being configured to store an item. The dispensing unit may also include a cover coupled with the housing and extending between the first end and the second end such that the cover is positioned over the plurality of compartments and an actuator coupled with the cover. The actuator may be configured to retract the cover to draw a leading edge of the cover from the first end toward the second end to expose a selected number of the plurality of compartments.

In another embodiment, a method of operating a dispensing mechanism is provided. The method may include receiving an input to dispense a selected number of items from a secure dispensing mechanism and actuating a cover of the secure dispensing mechanism to retract a leading edge of the cover to expose a selected number of compartments of the secure dispensing mechanism based on the selected number of items. The number of compartments may be arranged linearly along an axis of the secure dispensing mechanism, with each of the compartments being configured to store an item.

In another embodiment, a cabinet is provided. The cabinet may include a housing defining a storage region and at least one drawer. Each of the at least one drawer may include a first side and a second side and a plurality of compartments arranged linearly along an axis of the at least one drawer. Each of the compartments may be configured to store an item. The at least one drawer may also include a cover coupled with the housing and extending between the first side and the second side such that the cover is positioned over the plurality of compartments and an actuator coupled with the cover. The actuator may be configured to retract the cover to draw a leading edge of the cover from the first side toward the second side to expose a selected number of the plurality of compartments.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 10A illustrates an empty cassette according to embodiments of the present invention.

FIG. 10B illustrates the cassette of FIG. 10A in a filled state.

DETAILED DESCRIPTION OF THE INVENTION

Figure 1:
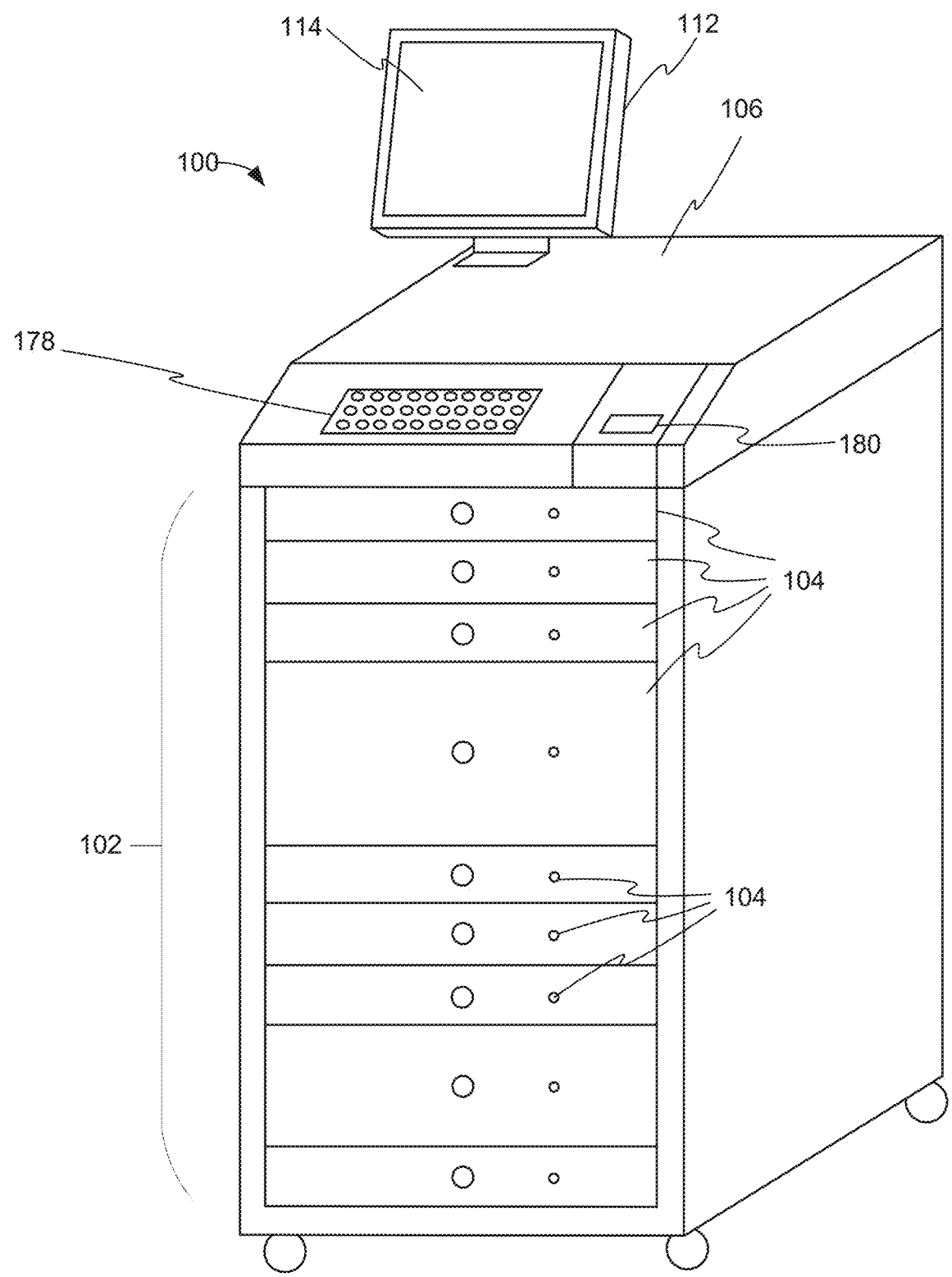
FIG. 1 illustrates an example cabinet in which the invention may be embodied.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims. Merely by way of example, any embodiment described herein may or may not have any of the features discussed therewith, and may or may not have any feature discussed with respect to other embodiments.

Embodiments of the present invention are directed to dispensing mechanisms that provide controlled access to items stored therein. Embodiments of the invention include one more drawers or other storage units which each include a number of interior compartments that are usable to store one or more items, such as medications, tools, instruments, etc. Each drawer includes at least one cover that extends over at least some of the interior compartments. The cover may be retractable to provide selective access to a number of items and/or interior compartments. In some embodiments, the secure dispensing mechanism may be able to determine whether a particular compartment is empty and use this information to adjust a retraction distance of the cover to ensure access to the desired number of items is provided. For example, if a drawer includes a row of ten compartments that each include a single item and a user wishes to access three items, the dispensing mechanism may check to see if any of the compartments are empty by using one or more sensors, such as optical sensors, radio frequency (RF) sensors, load sensors, and the like. For example, if each of the ten compartments includes an item, the dispensing mechanism may retract the cover sufficiently far to provide access to the first three compartments, thereby allowing the user to remove the three items as requested. In another situation, the dispensing mechanism may determine that the first two compartments are empty and may then retract the cover sufficiently far to provide access to the first five compartments (including the two empty compartments), thereby allowing the user to remove the three items as requested.

Typically, the actuation of the cover is done while the drawer is in a closed position. By limiting the operation of the cover in such a manner, pinch points and/or other safety concerns are eliminated, as there are no moving parts once the drawer is open and available for user access. In operation, the user may interact with an interface of the dispensing mechanism to select a desired number of a particular type or types of items while the drawer is closed. The dispensing unit may then actuate one or more covers that correspond to a drawer and/or compartments within which the particular items are stored to retract each respective cover a proper distance to provide access to only those items that have been previously selected. Once the covers have been retracted, the relevant drawer or drawers may be unlocked, allowing the user to open the drawer and access the items within compartments which have been exposed by the retraction of the cover. After the items are removed, the user may shut the drawer. In some embodiments, the exposed compartments, now empty, may remain exposed, with the cover remaining partially retracted. In other embodiments, upon which the secure dispensing unit may lock the drawer and actuate the cover to extend the cover back over the previously exposed compartments. This may be particularly useful if some or all of the compartments include multiple items. For example, if only a single item is taken from a compartment having two items, the cover may be retracted to cover the remaining item. Oftentimes, during the retraction and/or extension of the cover, one or more optical sensors positioned on the cover may be used to monitor an inventory of items within the compartments.

Turning now to the drawings and referring first to FIG. 1, a cabinet 100 that may serve as and/or house a dispensing mechanism is illustrated (although it will be appreciated that the dispensing mechanisms may be embodied in non-cabinet forms, such as carts, built in shelving/drawers, and the like.). Here, cabinet 100 includes a storage area 102 that is used to store any number of items, such as tools, instruments, paints, medications, medical supply items, and the like. As illustrated, the storage area 102 defines an open interior that is configurable to receive a number of drawers 104 that may serve as dispensing units, including some drawers 104 that are secured storage units. In some embodiments, the use of other storage areas such as shelves, racks, and the like are possible in addition to, or as alternative options to, drawers 104. In some embodiments, the cabinet 100 may include one or more lockable doors (not shown) that control access to the storage area 102. Thus, a lockable door or doors could be provided in addition to, or as an alternative to, drawers 104. Drawers 104 may be of different sizes and shapes to perform different functions and/or to accommodate items of various sizes and/or shapes and/or to accommodate various equipment, such as sensors, security features, climate control equipment, and the like. As illustrated, different sizes of drawers 104 may be included in a single cabinet 100. In other embodiments, a cabinet 100 may include drawers 104 of uniform sizes. It will be further appreciated that a cabinet 100 may include drawers 104 of uniform function and/or interior configuration or may include one or more drawers 104 that have a different function and/or interior configuration than other drawers 104 in the cabinet 100.

In some embodiments, the cabinet 100 may include a work surface 106. The work surface 106 may provide an area for the user to set items on during preparation or completion of a particular procedure. For example, the user may lay out some or all the of the items needed for the procedure on the work surface 106. In some embodiments, the work surface 106 may be a top surface of the cabinet 100, while in other embodiments, the work surface 106 may positioned at an intermediate height of the cabinet 100. Additionally, while illustrated as forming substantially all of the top surface of the cabinet 100, it will be appreciated that in some embodiments, the work surface 106 may not be present or may take up only a portion of the footprint of the cabinet 100.

The cabinet 100 may also include and/or be in communication with a computing device 112. The computing device 112 may include and/or be communicatively coupled with a display screen 114 and at least one input device. While illustrated with the display screen 114 coupled with the work surface 106 of the cabinet 100, it will be appreciated that in some embodiments the display screen 114 may be integrated into a body of the cabinet 100 and/or positioned at other locations (such as extending laterally from or sitting atop a nearby structure) relative to the cabinet 100. The input device 178 may include a keyboard, mouse, credential reader, microphone, camera and/or other device that enables a user to interact with the computing device 112. In some embodiments, a credential reader may include a wireless reader, such as a Bluetooth, RFID, NFC, and/or other wireless reader that may read information from an active or passive user credential, such as a fob, mobile phone, ID, and/or other credential device. In other embodiments, the credential reader may include a contact reader, such as a chip or magnetic stripe reader. In yet other embodiments, the credential reader may include a biometric reader 180, such as a camera or other optical sensor for facial, iris, and/or palm vein authentication, a microphone for voice authentication, a fingerprint reader, and/or other biometric sensor. In some embodiments, an input device may be incorporated into the display screen 114 by using a touchscreen display screen 114.

The input devices of computing device 112 allows a user to interact with the cabinet 100. For example, the user may interact with the input devices to log in, select a patient and/or procedure, and/or gain access to items stored within the cabinet 100. For example, to log in to the cabinet 100, a user may enter a user name, password, and/or other access credential (which may include a biometric credential) into the computing device 112 to verify that the user is authorized to access the cabinet 100 and/or a particular item stored therein. In other embodiments, a user may be logged in automatically if a wireless credential of the user is brought within range of a wireless credential reader of the computing device 112. Once a user is logged into the computing device 112, a graphical user interface (GUI) may be presented on the display screen 114 that allows the user to make selections about a patient, procedure, and/or items to be removed or otherwise dispensed from the cabinet 100. These selections may be made using any of the input devices of the computing device 112. In other embodiments, rather than navigating a GUI to make patient, procedure, and/or item selection, the user may use alternative selection means, such as voice commands, to make the necessary selections. In some embodiments, computing device 112 may include a network interface that enables the computing device 112 to communicate with a server and/or other remote computing device. The computing device 112 may use this connection to send an inventory of the cabinet 100 to the remote computing device. Such inventory counts may be updated periodically, such as every hour, work shift, day, etc. In other embodiments, the inventory may be tracked continuously before, during, and/or after each interaction with the cabinet 100. In some instances, the central pharmacy may initiate a remote inventory scan of the cabinet 100 by sending a command to the computing device 112 that causes the computing device 112 to gather and/or send inventory information to the remote computing device. Such inventory information may be usable by the remote computing device to determine when to refill and/or reorder a particular item. In some embodiments, the functions performed by computing device 112 could be performed by a remote server or other computing device over a network.

Once the user has selected which items are to be removed from the cabinet 100, the cabinet 100 may provide access to the items, such as by unlocking a drawer 104 and/or otherwise providing access to the storage area 102. Before, during, and/or after the user has removed any items from the cabinet 100, the computing device 112 and/or other computer system may use any number of sensors to monitor which items were actually removed from the cabinet 100. In some embodiments, the items that are actually removed are correlated with the items that the user originally selected for removal using the GUI. Such sensors may involve sensors integrated into the drawers 104 and/or those integrated into the work surface 106. In some embodiments, if there is a discrepancy between selected items and the items removed, an indication of the discrepancy may be stored and/or sent to another device, as such behavior may be indicative of diversion behavior, improper use of the items, and/or other improper usage of the cabinet 100. The indication may include information such as which user selected the items and which items were taken that did not match the selections.

Drawers 104 may be under the control of a computing device 112 and/or another controller. For example, each of drawers 104 may include an electronically controllable locking mechanism, and may only be openable under the control of computing device 112. In some embodiments, some or all of the drawers 104 may be temperature and/or humidity controlled. In addition, computing device 112 may store information about what supplies are stored in which compartments of cabinet 100. In one typical basic medical usage scenario, a health care worker may enter, using input device 178, an identification of a patient who is under the care of the health care worker, and who will need medication during the worker's current rounds. Computing device 112 may access the patient's medical file and determine what medications have been prescribed for that patient. In other embodiments, a user may merely select one or more items to remove from the cabinet 100, without the need to compare the data to an order, such as a patient treatment plan.

Once the items are selected, computing device 112 may unlock one or more drawers 104 (and/or doors, if used) that are associated with the selected items. In some embodiments, one or more lighted indicators may direct the healthcare worker to a correct drawer 104. A particular compartment within the correct drawer 104 may be highlighted, for example with a lighted indicator, to draw the user to the correct items. The user can then remove the selected items. In medical applications, the level of control exercised by computing device 112 may help in preventing medication and dosing errors, by reducing the likelihood that a health care worker will remove an incorrect medication from cabinet 100. In addition, in all applications computing device 112 may document and record which items were dispensed, and may forward that information to inventory and/or accounting systems.

Figure 2:
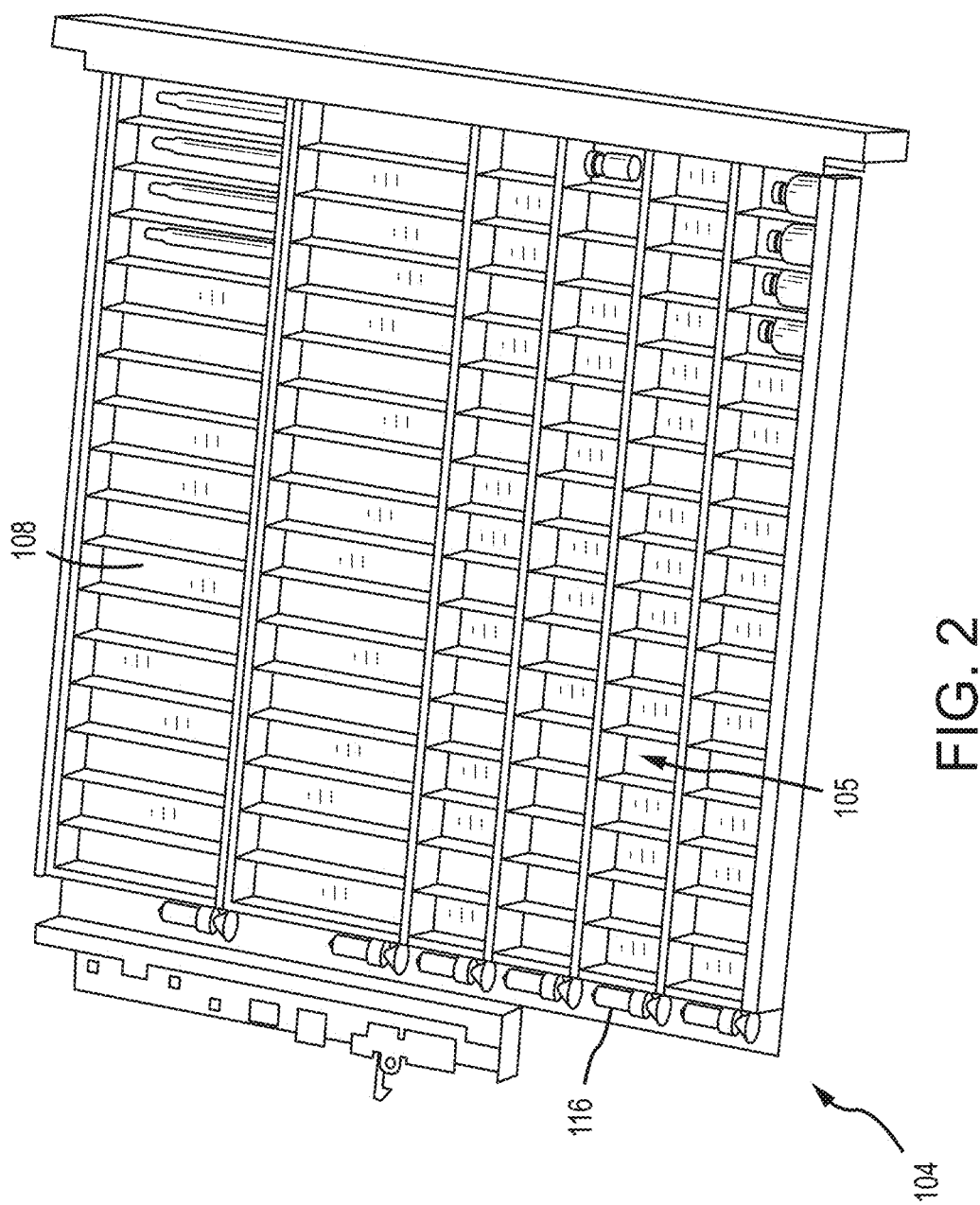
FIG. 2 illustrates a drawer defining a number of compartments according to the present invention.

Each drawer 104 may define a storage area in which one or more items may be placed. In some embodiments, the storage area may be a large open space, while in other embodiments the storage area of drawer 104 may be divided into one or more compartments or bins. For example, as illustrated in FIG. 2, a single drawer 104 is shown. The drawer 104 may be adapted to fit the cabinet 100 as shown in FIG. 1. The drawer 104 may include a storage area 105 that includes a number of bins or compartments 108 (which may or may not be formed as part of the drawer 104). In some embodiments, the size of the compartments 108 may be uniform, while in other embodiments compartments 108 of different sizes and/or shapes may be included in a single drawer 104 to allow the drawer 104 to more efficiently store a number of different items. While in some embodiments each compartment 108 may be sized and/or shaped to hold only a particular item, it is possible in other embodiments that multiple items may be placed in a single compartment 108. For example, multiple items may be stacked vertically, placed side by side, and/or placed top to bottom within a single compartment 108. As illustrated, drawer 104 includes a number of compartments 108 arranged in rows, with all the compartments 108 in a given row being identical.

Figure 3:
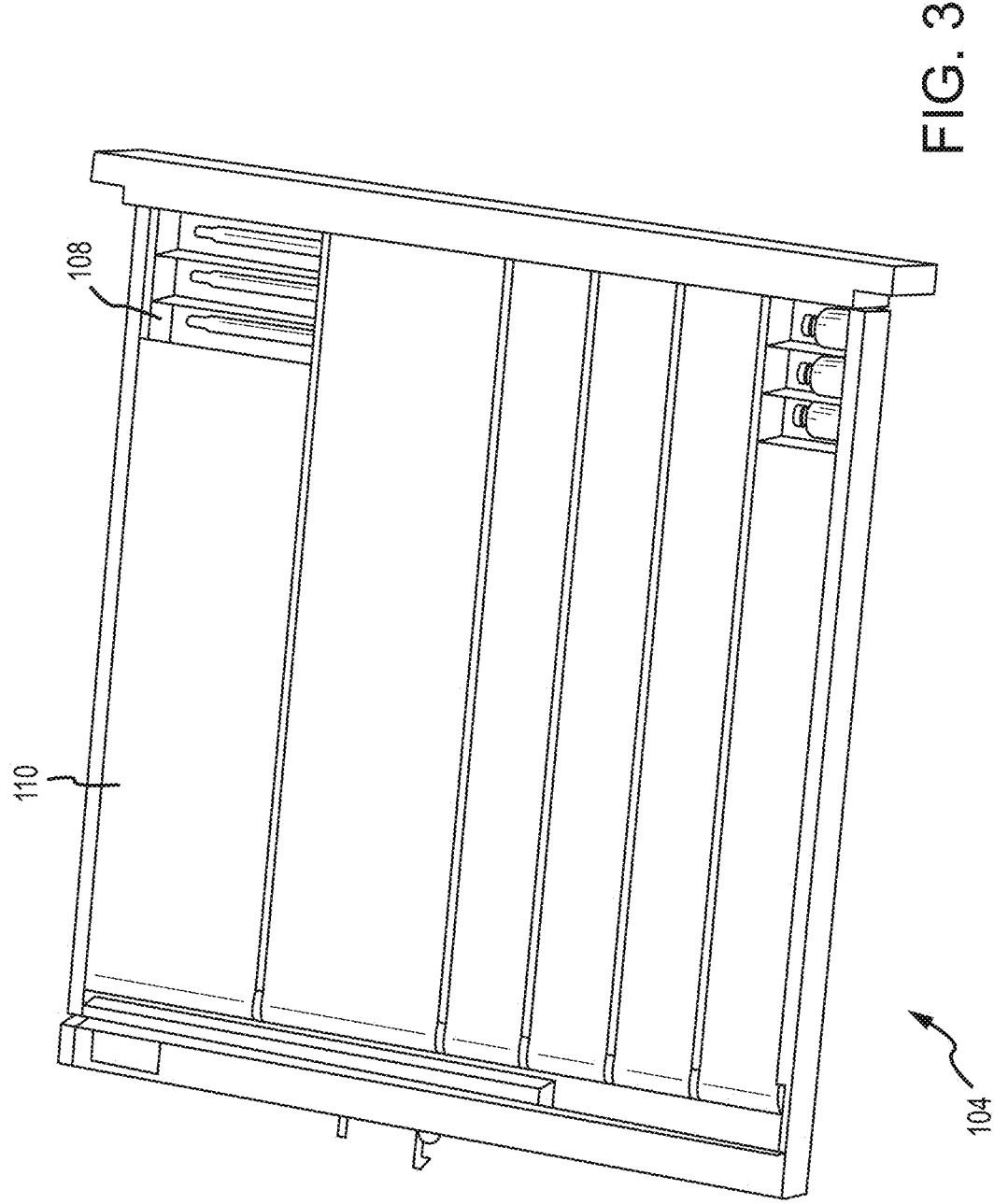
FIG. 3 illustrates a retractable cover interface with the drawer of FIG. 2.

In some embodiments, drawer 104 may include a cover 110 that extends over at least some of the compartments 108 in a drawer 104. For example, as illustrated in FIG. 3, a number of covers 110 are provided that extend across an entire row of compartments 108. Here, the entire row of compartments 108 are oriented between front and back ends of the drawer 104. In other embodiments, an entire row of compartments 108 may be oriented between the sides of the drawer 104. In some embodiments, covers 110 extend across the entire row. In other embodiments one or more covers 110 may extend across any portion of a row of compartments 108. In some embodiments, one or more covers 110 may extend over one or more of the compartments 108 in more than one row. In some embodiments, rather than having covers 110 atop every row of compartments 108, one or more of the rows of compartments 108 may be open-topped such that a user may access contents of the open-topped compartments without the need to retract a cover 110. Each cover 110 may be configured to be retracted to expose a selected number of compartments 108 and/or items. The cover 110 encloses the compartment 108 such that any item present within the compartment 108 may not be accessible to permit retrieval of the item. The cover 110 is moveable using suitable actuation mechanisms so that any particular compartment 108 may be uncovered to allow retrieval of an item stored within the compartment 108. In one example, each of the one or more compartments 108 may be uncovered in a sequence, such that all compartments 108 that have been previously uncovered remain uncovered. In another example, the cover 110 may allow only one compartment 108 to be uncovered at any given time and for the rest of the compartments 108 associated with that cover 110 to be enclosed by the cover 110. An actuator 116 (as shown in FIG. 2) may be coupled with each of the covers 110 such that the covers 110 may each be actuated to extend and/or retract the covers 110 independently of one another. In some embodiments, a single actuator may be used to move multiple covers 110, while in other embodiments each cover 110 may include a dedicated actuator 116. This ensures that if a user wants an item in a particular row of compartments 108, only items from that row are exposed when the user accesses the drawer 104. In addition to controlling access to non-selected items, by retracting covers 110 of only compartments 108 and/or items that are selected by the user prior to access, the user is able to quickly identify the items for removal, as the selected items will be the only ones that are not covered.

In embodiments that utilize drawers 104 with retractable covers 110, once the user makes his selection of one or more items to retrieve from the cabinet 100, the computing device 112 identifies one or more drawers 104 and/or compartments 108 that are associated with the selected items. The computing device 112 may then send a signal to an actuator 116 associated with the relevant compartments 108. The signal causes the relevant actuators 116 to activate to retract an attached cover 110 to expose a number of compartments 108 necessary to dispense the correct number of selected items. In some embodiments, multiple actuators 116 and covers 110 may be actuated in one session (either simultaneously or in sequence) to provide access to items in different rows and/or drawers 104. Once the relevant covers 110 have been actuated, the relevant drawers 104 may be unlocked, allowing the user to access the drawers 104 and exposed compartments 108. Once the user is done removing items, the user may close the drawer 104. Once the computing device 112 detects that the drawers 104 are closed (such as by using one or more door close sensors) the computing device 112 may lock each drawer 104 and subsequently activate the actuators 116 to extend the cover 110 over the exposed compartments 108. In such a manner, the cabinet 100 may prevent the possibility of any pinch points that may be created while the covers 110 are being moved, as the covers 110 are only moved when the drawers 104 are closed and/or locked.

In some embodiments, some or all of the drawers 104 may include one or more sensors that track the inventory and usage of items stored within the drawers 104 and/or compartments 108. Such sensors may be specific to a particular drawer 104, bin/compartment 108, cassette, and/or portion thereof. In other embodiments, a single sensor and/or group of sensors may be used to monitor multiple drawers 104, bins, and/or cassettes, and possibly an entire interior of the cabinet 100. It will be appreciated that various arrangements and designs of drawers 104 may be used in conjunction with cabinet 100.

Know the User

As discussed above, many applications of secure dispensing units, such as cabinet 100, may require that a user provide authentication credentials in order to access the cabinet 100. Several types of access credentials may be utilized. In some embodiments, logging in may be done by a user entering access credentials, such as a user name, password, and/or other credential. However, it may be desirable for a user to gain access quicker and/or easier than is achievable with manually keying in access credentials into a keyboard, keypad, and/or touchscreen. In such embodiments, other forms of access credentials may be utilized. For example, possession-based credentials may be utilized. In some embodiments, a possession-based credential may be in the form of a universal serial bus (USB) dongle, chip card, magnetic stripe card and/or other device that may be inserted into a port of a credential reader and/or otherwise scanned by a credential reader of the computing device 112. Once inserted or read by the computing device 112, the credential device may be authenticated to provide access to the patient, procedure, and/or item selection systems and may retrieve one or more items from the cabinet 100. The authentication of the access credentials (possession-based, knowledge-based, and/or biometric) may be performed locally by the computing device 112 and/or may be performed remotely. When performed remotely, the authentication may involve the computing device 112 capturing the credentials and sending the credentials to a remote device, such as a backend server, for subsequent authentication. A result of the authentication of the credentials may be sent back to the computing device 112, which will then control access to the functionality of the cabinet 100 based on the result.

In other embodiments, a possession based access credential may be in the form of a contactless device, such as a radio frequency (RF) wireless device that may be wirelessly read by a credential reader of the computing device 112. For example, the credential may be in the form of a card (such as an employee identification card), mobile phone, wristband, watch, other wearable, and/or other high integrity possession-based authentication object that may have an integrated RF chip. This enables the user to approach the cabinet 100 while in possession of one of these RF-enabled access credentials and gain access to the cabinet 100 with little to no log in action necessary by the user. For example, the RF-enabled access credential may include a Bluetooth® enabled device, RFID chip or tag, and/or other short range RF communication protocol that enables the access credential to be read by the credential reader of the computing device 112 as soon as the user is within a signal or detection range of the credential reader. In other embodiments, the access credential may operate using a shorter range communications protocol, such as near field communication (NFC). In such embodiments, the user may need to actively bring the access credential within signal range of an NFC credential reader of the computing device 112.

In some embodiments, the RF chip of the access credential may be a passive chip that is powered by electromagnetic energy transmitted from an RFID reader/antenna of the credential reader of the computing device 112. In other embodiments, the access credentials may include active RFID chips or tags that are powered by a battery (either a dedicated battery or a battery of a device containing the RFID chip or tag) continuously broadcast a signal containing the necessary access credentials for a particular user. Typically, such active RFID tags have a longer range at which the data can be read than the passive RFID tags. In some embodiments, the credential reader of the computing device 112 may be designed to have a predetermined signal/detection range that ensures that a user is sufficiently close to the cabinet 100 prior to reading a possession-based access credential. For example, a signal strength of the credential reader and/or RFID tag may be adjusted such that a desired signal range is achieved that helps prevent the computing device 112 from attempting to log in multiple users or an incorrect user when multiple people are positioned proximate the cabinet 100. In other embodiments, the range of the cabinet 100 may be limited to a particular room or area in which the cabinet 100 is located. For example, RF shielding and/or other materials may be provided around a periphery of the room to ensure that only access credentials within the room may be detected by the credential reader of the cabinet 100.

In some embodiments, rather than using a knowledge-based or possession-based access credential, the cabinet 100 may include one or more biometric readers that enable users to log in without carrying a physical access credential device. For example, the computing device 112 of cabinet 100 may include or be communicatively coupled with a fingerprint reader, a speaker for voice recognition, one or more optical sensors (such as a cameras, infrared (IR) scanners) for iris scanning, facial detection, palm vein recognition, and/or other biometric authentication techniques.

When using biometric authentication techniques that involve imaging a portion of a user (such as, but not limited to, facial recognition) anti-spoofing measures may be taken to help thwart fraudulent authentication attempts, such as when one user attempts to present a photograph, video, and/or mask of a different person who is an authorized user of the cabinet 100 to an image sensor of the cabinet 100. Such anti-spoofing measures may include, for example, active face liveness detection and/or passive face liveness detection. For active face liveness detection, the user may be asked to perform a specific action, such as nodding, blinking, smiling, and/or other facial pattern or gesture. If the computing device 112 determines that the user has performed the requested action, the computing device 112 may determine that the user being imaged is real and may be authenticated properly. In some embodiments, the facial pattern or gesture may be the same each time a user logs on, while in other embodiments, any number of facial patterns and/or gestures may be cycled through and/or randomly assigned to a particular login attempt. Using multiple facial patterns and/or gestures adds an additional layer of security that helps prevent videos from being displayed to the camera of the computing device 112 in an attempt to fraudulently login to the cabinet 100.

Passive face liveness detection may involve various techniques. For example, some embodiments may utilize face flash liveness which uses a light element to illuminate the user (or copy of the user). The reflectance of the user is measured, allowing the camera to capture how the light from the screen and/or other light source reflects on the face. The computing device 112 can then determine whether the illuminated face belongs to a live person or a reproduction (such as a photo or a video) based on the measured reflectance. Some embodiments may perform passive face liveness detection using eye blink detection. For example, blinking by the user may be detected and timed. If no blinking is detected and/or the detected blinking is performed at a rate that is not common, the computing device 112 may deem the authentication attempt to be based on a reproduction of a user. Some embodiments may employ the use of trained convolutional neural networks (CNNs) to detect the authenticity of a user detected by a camera of the computing device 112.

Additional passive anti-spoofing techniques may involve the use of infrared and/or 3-dimensional cameras, which may be able to readily distinguish between human users and reproductions such as 2-dimensional photographs and/or videos, as well as both 2-dimensional and 3-dimensional masks. For example, 3-dimensional cameras may be able to measure the depth of various features of an image and be abler to distinguish between flat objects (e.g., photographs and/or display screens that may be showing a user's image) and 3-dimensional objects (such as a user or 3-dimensional mask). IR cameras (or other IR sensors) are capable of determining whether an image being detect has a thermal profile that matches that of a specific user and/or generally matches that of a human. For example, the thermal profile of a photo or display screen will not match that of a human. Similarly, both 2-dimensional and 3-dimensional masks will not have a thermal profile similar to a human unless a very sophisticated mask is utilized.

The use of voice recognition as an access credential typically involves a user speaking a particular word or phrase into a speaker of the cabinet 100. The user's voice signature (tone, pitch, cadence, etc.) may be compared to a previously stored voice signature of known authorized users in order to detection where the user can be authenticated. In some embodiments, rather than having a user speak a same predetermined word or phrase, the cabinet 100 may prompt the user to speak a random one of a number of words or phrases in order to reduce the likelihood that someone could create an audio recording of an authorized user speaking a predetermined passphrase.

In some embodiments, multiple forms of credentials may be required to log in to further enhance the security of the cabinet 100. For example, a physical access credential may be a chip card that requires the user to enter a personal identification number (PIN) in order to log in. Such embodiments require that the user have both possession of an access credential and knowledge of an alphanumeric login credential in order to be logged into the cabinet 100. In other embodiments, the cabinet 100 may require both a biometric credential (such as facial recognition) and a physical credential (such as a contactless credential device) in order to log into the cabinet 100. It will be appreciated that any combination of knowledge-based, possession-based, and/or biometric access credentials may be utilized to meet the security needs of a particular application. Additionally, in some embodiments, multiple types of a single type of credential may be utilized. For example, multiple forms of biometric credentials may be utilized (such as fingerprint and voice) to help further reduce the likelihood of fraudulent authentication.

Additionally, in some embodiments, backup authentication means (biometric and/or otherwise) may be assigned in the instance that a particular access credential is not available at a particular time. For example, if a user has a respiratory illness and cannot speak or can only speak with noticeable changes to his voice, an alternative to a voice recognition system (such as an alternative biometric credential, a knowledge-based credential, and/or a possession-based credential) may be utilized. Similarly, if a possession-based credential is not available, such as if an RF chip is not functioning properly or a user forgets a physical access credential, the cabinet 100 may provide an alternative authentication process that does not involve the unavailable access credential device. In some embodiments, a user may select an alternative authentication process, while in other embodiments such processes may be automatically provided by the cabinet 100 upon one or more failed attempts at successful authentication.

In one particular application, the cabinet 100 may be utilized as a cart for a physician, such as an anesthesiologist. Oftentimes, such personnel often have a need to access medications and/or equipment stored within a cabinet 100 quickly. Additionally, these users typically do not view the tracking of inventory as part of their duties. As a result, in such applications the cabinet 100 may be operated in a manner that ensures that the user may be logged on quickly and efficiently, with as little interaction as possible by the user. For example, in such embodiments the cabinet 100 may require hands free authentication credentials, such as possession-based wireless and/or contactless credential devices and/or biometric authentication credentials. Oftentimes, there may be a desired to utilize a contactless biometric authentication credential (i.e., not fingerprint) as such contact may be time consuming and/or less ergonomic than contactless biometric credentials. As a result, a cabinet 100 for a physician-based application may be configured to utilize facial, iris, palm vein, and/or voice credentials as login credentials. Additionally, hands free authentication credentials (possession-based and/or biometric-based) may be particularly useful in applications in which some or all of the users will be accessing the cabinet 100 with gloved hands, as gloves may make it more difficult for a user to key in access credentials, manipulate a contact-based credential device, and/or supply contact-based biometric credentials such as fingerprints. While discussed with using hands free authentication credentials for cabinet 100 that are accessed by physicians, it will be appreciated that in many applications authentication forms that require user actions and/or hand usage may be utilized in some embodiments.

Selecting an Item

Once a user is logged into the cabinet 100, the user may be prompted to enter additional details regarding what items are to be removed. For example, one or more items may be associated with a particular location and/or task. The selection may include what type and how many items are to be removed, possibly along with a particular task, location, and/or other information associated with the use of the item. This information, along with the knowledge of which user logged into the cabinet 110, allows the computing device 112 to track which user used each item and for what purpose. This may be particularly relevant in medical applications in which medications and/or other medical items are to be used in conjunction with a particular treatment and/or a particular patient. To enter these details, a user may interact with the computing device 112 using one or more input devices, such as a keypad, a keyboard, a mouse, a touchscreen display 114, and/or other input device. In some embodiments, the selection procedure may be voice controlled such that a user may select one or more items, tasks, patients, etc. Oftentimes, voice controlled systems may also include a manual entry selection system as a backup in case the voice control system is not functioning properly or in the event that a user has a respiratory illness or other cause of voice change or voice loss that may make it difficult to operate a voice controlled selection system.

In some embodiments for medical applications, a procedure list may be provided to the cabinet 100 that includes a limited number of patients, procedures (e.g., treatments), locations, personnel (nurses, techs, physicians, orderlies, etc.) to choose from. In some embodiments, the procedure list may be populated by scanning information from a patented wristband, chart, and/or other data source. In some embodiments, the procedure list may be manually populated at the cabinet 100 and/or at a remote computing device that then communicates the procedure list to the cabinet 100. In other embodiments, the procedure list may be automatically populated using a hospital (or other facility) scheduling system. For example, an electronic health records (EHR) system may be used to automatically populate the procedure list with data regarding specific patients and/or procedures that are currently on a schedule. In some embodiments, the EHR system may utilize knowledge about where a particular cabinet 100 is located in order to populate the procedure list. For example, if a cabinet 100 is located in an intensive care unit (ICU), the procedure list for the cabinet 100 may only be populated with only patients and/or procedures that correspond to patients present in the ICU, procedures performed in the ICU, and/or medical personnel staffing the ICU. Similarly procedure lists may be provided for each cabinet 100 in a designated area of a facility (NICU, maternity ward, operating room, etc.). In other embodiments, a cabinet 100 may include a procedure list that contains data about each patient and/or scheduled procedure in an entire facility. In other embodiments, the precede list may be populated with any procedure that may be performed in the facility, regardless of likelihood or location of the cabinet 100. The procedure list for a given cabinet 100 may be presented on a GUI displayed on the display screen 114, allowing a logged in user to access the procedure list and make selections of items to access for one or more patients and/or procedures.

In some embodiments, a location of the cabinet 100 may be preprogrammed into the cabinet 100 (such as by tagging the cabinet 100 as being associated with a particular facility and/or portion thereof.). In other embodiments, the EHR system and/or other central computing system may be programmed with a location of each respective cabinet 100 in a given facility. For example, a location may be associated with a serial number and/or other unique identifier of the cabinet 100 such that the EHR system has knowledge of the location of each cabinet 100 in a facility. In other embodiments, the location may be determined based on a wireless connection (such as a Bluetooth beacon) and/or other RFID tag that is usable to determine a location of each cabinet 100 in a facility and associate the location with an identifier of the respective cabinet 100. In other embodiments, each cabinet 100 may include one or more other location determining features, such as a global positioning satellite (GPS) and/or other location sensor that may determine where in a facility the cabinet 100 is located.

In some embodiments, not only may a procedure list be populated based on a location and/or known patients and/or procedures, but the storage area 102 of the cabinet 100 may be populated with items, such as tools, medications, instruments, and the like based on the location and/or expected function of the cabinet 100. For example, in a neonatal ward, only items and/or medications (and doses) that are relevant to the treatment of infants may be stored within the cabinet 100. Similarly, a cabinet 100 in an operating room may be stocked with items and medications that may be used during surgical and/or other procedures. In some embodiments, such as where a procedure list is not used, is out of date, is incomplete, etc. a user may manually enter data about a patient and/or procedure into the computing device 112.

Logged in users may interact with the procedure list (or other selection menu) to select item criteria (patient, case, expected procedure, location, medical personnel, etc.) using the GUI presented on the display screen. For example, the user may select and/or key in any necessary data and/or selections using a physical input device of the computing device 112 and/or may navigate the selection process using voice commands.

In some embodiments, rather than needing to select a patient and/or procedure, once a user is logged into the cabinet 100 only an item to be removed need be selected. This may be particularly useful in non-medical applications and/or other applications that do not involve patients and/or recipients of a particular item in which the task being performed with a particular item may not need to be taken into account. While patients and/or other recipients may not be involved, the cabinet 100 may oftentimes still require a selection of a task, project, and/or location associated with the use of an item. For example, if a tool is being removed from an cabinet 100 in a construction application, the user may need to select a particular project that the tool is being used on. This ensures that not only may the use of the item be attributed to the logged in user, but also that a specific task may be associated with the tool, which may better help the usage of the tool be tracked. This may also make tracking down lost items easier, as a last known location and/or project associated with the item may be known.

In some embodiments, once a user is logged into the cabinet 100, the user may gain access to all of the contents within the storage area 102. In other embodiments, one or more users of the cabinet 100 may have clearance levels that provide access to only a subset of the storage area 102. For example, a nurse may have access to only non-controlled substances, while a physician may have access to an entirety of the storage area 102, including controlled substances such as narcotics. In some embodiments, such controlled items may be housed in separate containers (such as high security drawers 104) while in other embodiments controlled and non-controlled substances and/or other items may be stored within a single area, such as in a single drawer 104. In some embodiments, to further enhance security of these controlled items when placed in drawers with less secure items, the controlled items may be placed in lockable bins that are secured within and/or otherwise provided within a drawer 104 and/or other feature of the storage area 102. In some embodiments, the controlled items may be in compartments 108 that are secured by a retractable cover 110. In other applications, each user may have access to items that pertain to their particular job function and/or training specialties. For example, if a user has not been certified to administer a particular form of treatment and/or perform a type of procedure, the user may not be given access to portions of the storage area 102 that contain items that are used only in the particular treatment and/or procedure.

Access

Once a user has made selections about any items to be retrieved from the cabinet 100 (including any other data, such as patients, procedures, tasks, locations, personnel, etc.), the cabinet 100 may provide access to the interior of the storage 102 to allow the user to take the items that the user is authorized to possess and/or administer. In some embodiments, this may be achieved by the computing device 112 sending an unlock command to one or more drawers 104 positioned within the storage area 102. The unlock command may cause a locking mechanism, such as a solenoid-actuated lock, to disengage and allow the drawer 104 to be opened. In some embodiments, a cover 110 within a drawer 104 may be retracted to expose one or more compartments 108 to provide access to controlled items (such as narcotics).

Once the user gains access to the storage area 102 and may take the selected items. In some embodiments, multiple drawers 104 and/or other storage units may need to be accessed by a user to retrieve all of the items that have been selected for use. Once the items have been taken, the user may close the drawer 104 and/or other portion of storage area 102. The drawers 104 and/or other partitions may be locked again by the cabinet 100 to secure any remaining items within the storage area 102. Any retracted covers 110 may then be extended to again cover the exposed compartments 108.

Figure 4:
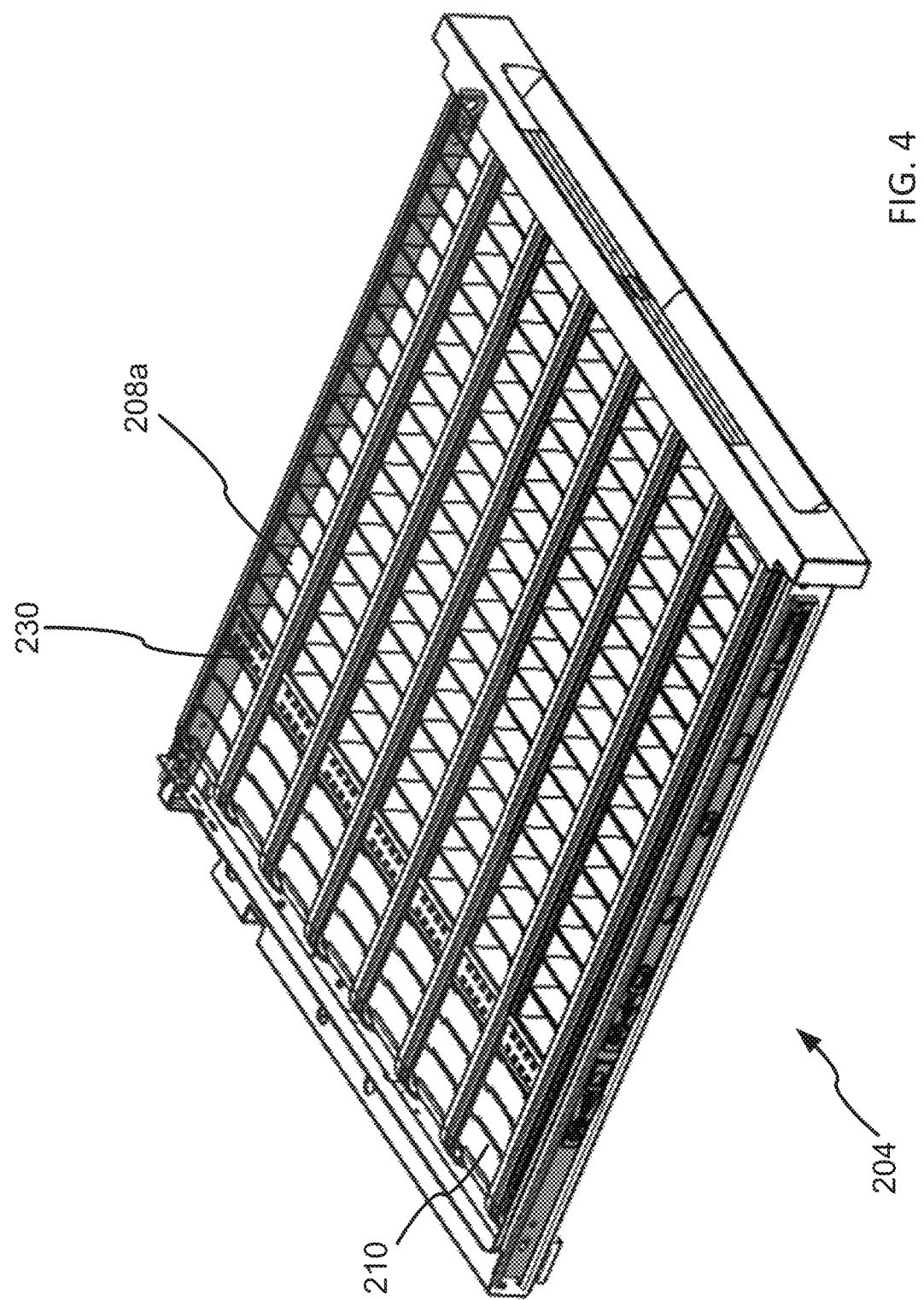
FIG. 4 illustrates an embodiment of a drawer that may serve as a secure dispensing unit according to the present invention.

Turning to FIG. 4, an embodiment of a drawer 204 that may serve as a secure dispensing unit is illustrated. In some embodiments, drawer 204 may be similar to drawer 104 and/or may be used in cabinet 100 described above. For example, drawer 204 include a storage area 206 that include a number of compartments 208a (which may or may not be formed as part of the drawer 204). While illustrated with the size of the compartments 208a being uniform, different sizes and/or shapes may be included in a single drawer 204 to allow the drawer 204 to more efficiently store a number of different items. Oftentimes, each compartment 208a may be sized and shaped to hold only a single item, however in some embodiments multiple items may be stacked, placed side by side, and/or placed top to bottom in a single compartment 208a. As illustrated, drawer 204 includes a number of compartments 208a arranged in rows, with all the compartments 208a in a given row being identical.

In some embodiments, drawer 204 may include a cover 210 that extends over at least some of the compartments 208a in a drawer 204. Here, each row of compartments 208a includes its own dedicated cover 210 that is configured to extend across an entire row of compartments 208a. Each cover 210 may be configured to be retracted to expose a selected number of compartments 208a and/or items and to be extended to recover the compartments 208a when access is no longer needed. The cover 210 may be a single piece of flexible material and/or multiple pieces of flexible and/or rigid material that are coupled together to form a length of material having a first end and second end. When decoupled from the drawer 204, the cover 210 may be extended into a single planar strip of material with the first end and second end at opposite ends of the length of the strip of material. The cover 210 is sufficiently strong to prevent users from accessing covered compartments 208a. In some embodiments, the cover 210 may be opaque to prevent covered compartments 208a from being viewable, while in other embodiments the cover 210 may be transparent to allow users to view the contents of covered compartments 208a.

Figure 5:
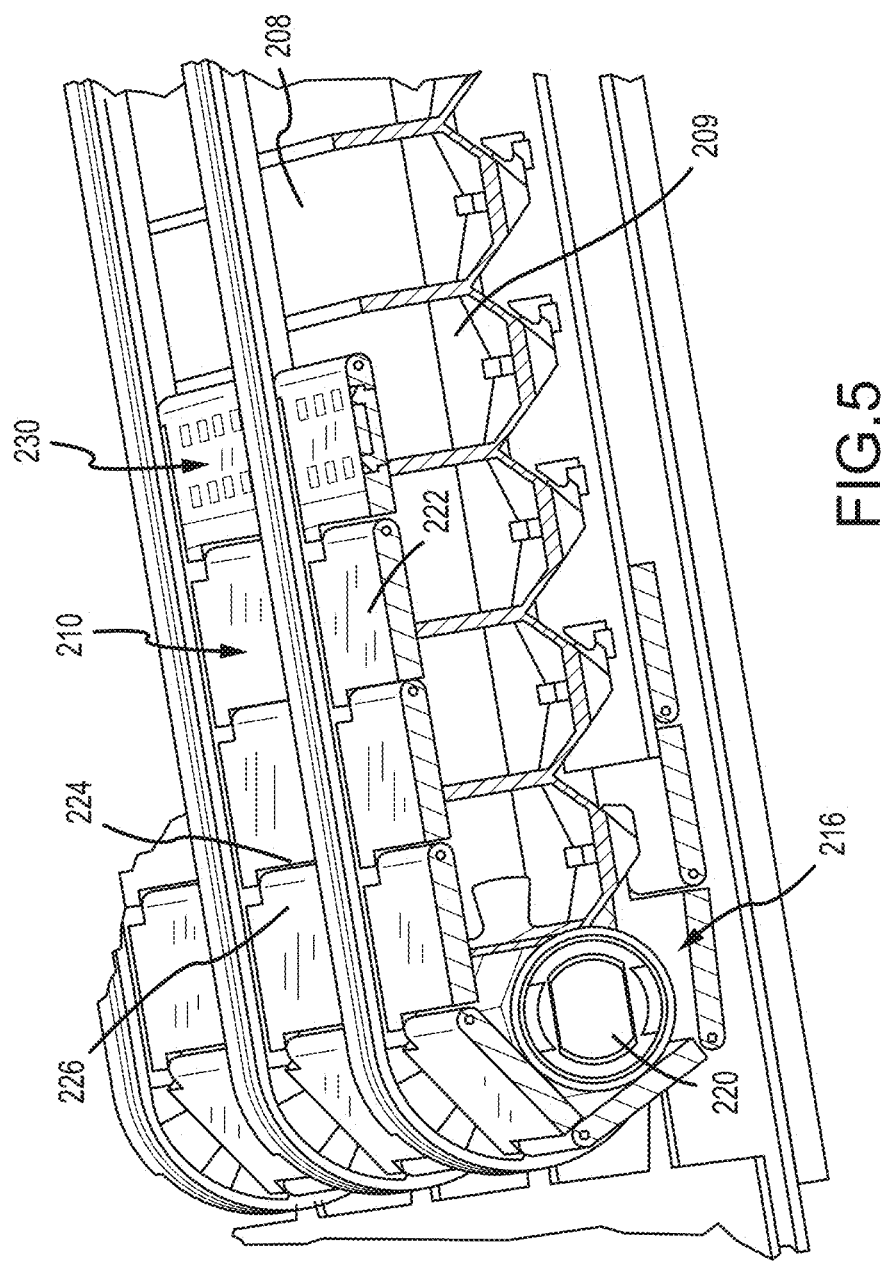
FIG. 5 illustrates a cover of the drawer of FIG. 4.

As indicated above, the cover 210 may be formed from a number of pieces of material. As best illustrated in FIG. 5, a number of segments 222 may be linked together similar to a watch band. For example, each segment 222 may include a female portion 224 at one end and a male portion 226 at the other end. As just one example, the female portion 224 may include a central recess formed between two extensions. The male portion 226 may include a central extension surrounded by two indented portions. The central recess of the female portion 224 may be slightly larger than the central extensions of the male portion 226 such that the central extension of the male portion 226 of a first segment 222 may be inserted into the central recess of the female portion 224 of a second segment 222. The extensions of the two segments 222 may then be pivotally coupled together to link the segments 222. For example, a pin 262 may be inserted through each segment to link the extensions of the segments 222 together. In such a manner, a number of segments 222 may be linked together in a manner that allows the linked segments 222 lengths of material that may be arranged in planar formations to cover the compartments 208a and/or curved to follow a curved movement path as the cover 210 is extended and/or retracted. In some embodiments, a portion of the cover 210 may be arranged in a planar manner while another portion of the cover 210 has segments 222 that are pivoted relative to one another to curve a portion of the cover 210. It will be appreciated that other designs of pivotable segments may be used to create the cover 210.

Figure 6:
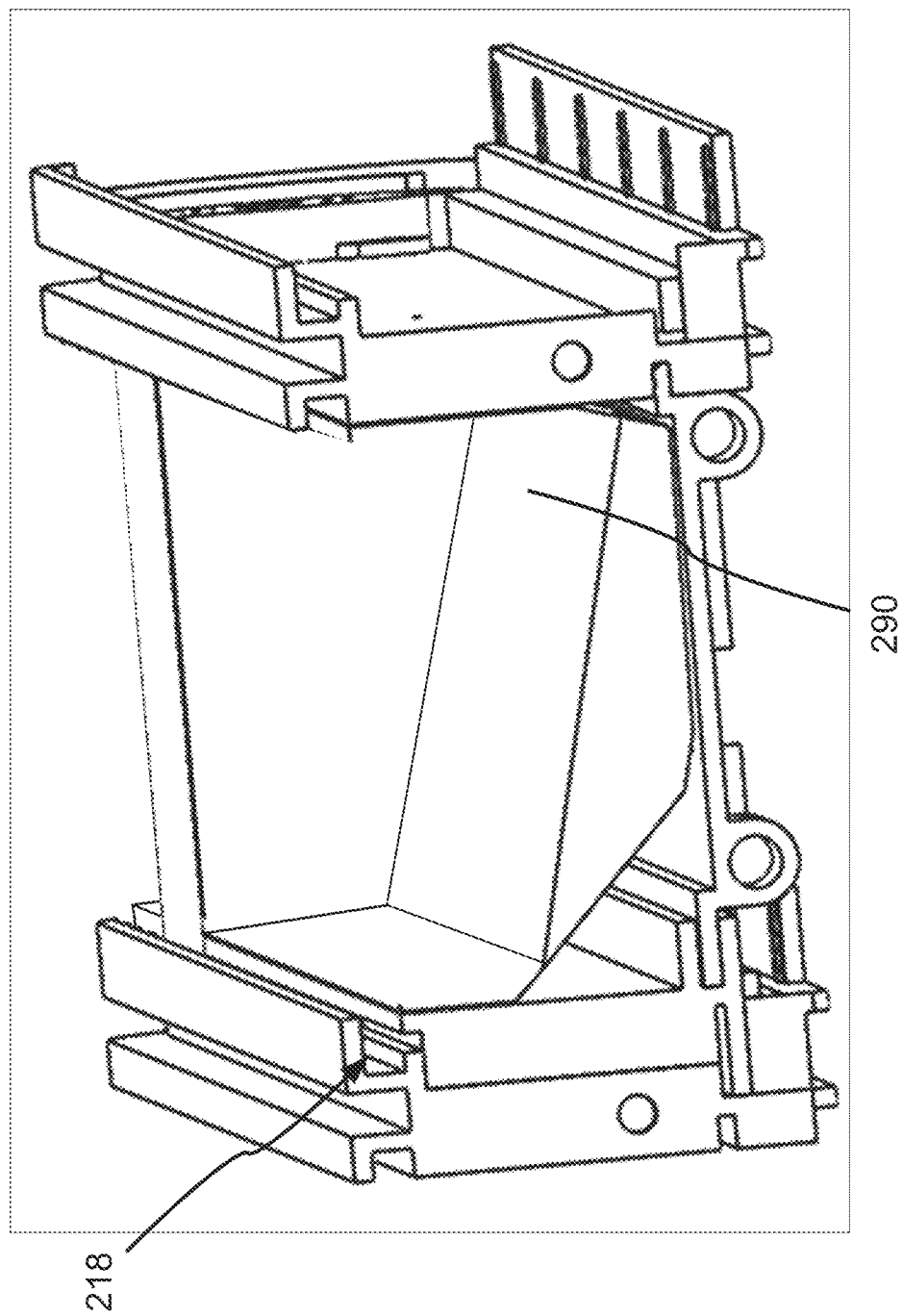
FIG. 6 illustrates a track to constrain movement of the cover of FIG. 5.

In some embodiments, a cover may be constrained to a particular movement path via one or more tracks formed in a given compartment. For example, as illustrated in FIG. 6, tracks 218 are formed in a compartment 290, which may be similar to compartment 208 described herein. The tracks 218 may be provided near top edges of each compartment 290 and/or row of compartments 290 that a cover (such as cover 210) is intended to secure. As illustrated, the tracks 218 are in the form of channels that receive lateral edges of the cover to ensure that the cover moves linearly along a longitudinal axis of the cover to cover and expose the compartments 290 and/or rows. The tracks 218 are positioned proximate a top of the compartments 290 so as to effectively seal compartments 290 that are below a position of the cover. While not shown, in some embodiments tracks 218 may be provided below the compartments 290, providing a movement path below the compartments 290 that enables the cover 210 to be drawn back and rolled under the compartments 290 in a manner similar to a roll top desk. In embodiments in which the cover is formed of linked segments (such as linked segments 222), as the cover is retracted and rolled back, some of the segments may be pivoted to curve and wrap around to move underneath the compartments 290.

Figure 7:
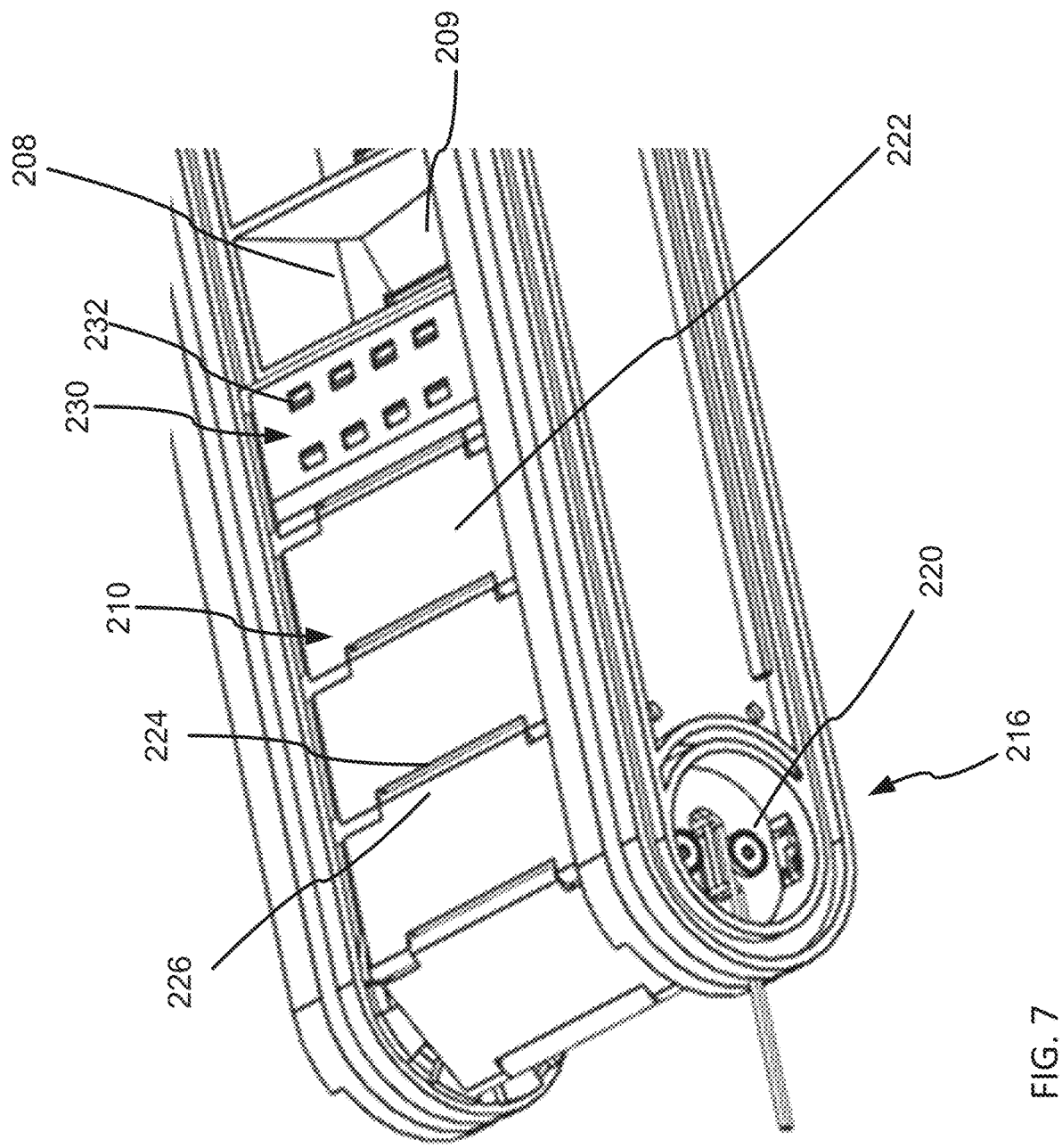
FIG. 7 illustrates an actuator of the cover of FIG. 4.
Figure 8:
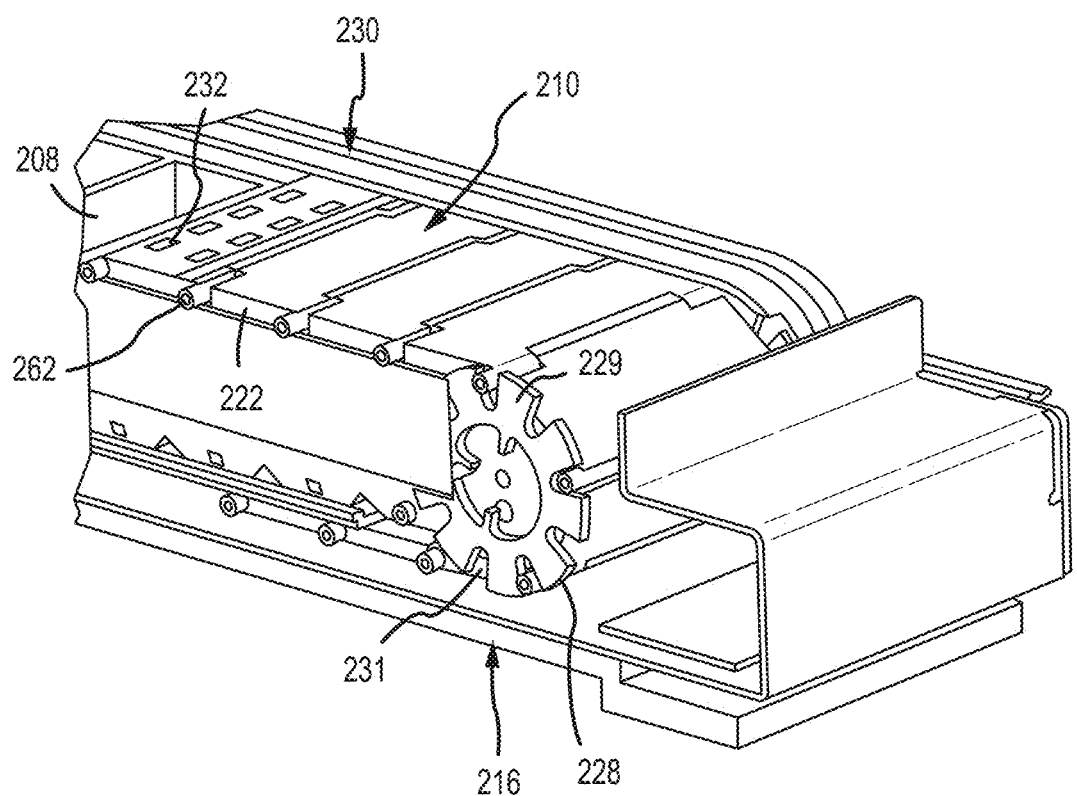
FIG. 8 illustrates a hub of the actuator of the cover of FIG. 7.

An actuator 216 may be coupled with each of the covers 210 such that the covers 110 may each be actuated to extend and/or retract the covers 210 independently of one another as best illustrated in FIG. 7. Oftentimes, the actuator 216 may include a motor 220 that is configured to generate force that may be applied to the cover 210. In some embodiments, the actuator 216 may include a transmission device that transfers the force from the motor 220 to the cover 210. For example, as illustrated in FIG. 8, the actuator 216 may include a hub 228 that coupled with edges of the cover 210. As illustrated, hub 228 includes a number of cogs 229 that are distributed radially about the outer periphery of the hub 228. In some embodiments, the pins 262 used to connect each segment 222 may extend laterally beyond the edges of the segments 222. Ends of each pin 262 may fit in spaces 231 between the cogs 229 of the hub 228, allowing the rotation of the motor 220 and hub 228 to retract and extend the cover 210 based on the direction of the rotation. In other embodiments, edges of the cover 210 (such as edges of each segment 222) may define apertures (not shown) that are configured to receive the cogs 229 of the hub 228 as the hub 228 is rotated by the motor 220.

In some embodiments, the motor 220 may include and/or be coupled with an encoder (not shown) that informs the motor 220 how many compartments 208 have been exposed. For example, the encoder may include information associated with a size of each compartment 208, a rotational speed of the motor 220, an effective radius of the transmission, and/or other information that may be usable to determine how far the cover 210 has been moved relative to the compartment 208. This ensures that the encoder is capable of allowing the motor 220 to actuate to move the cover 210 to positions in which a distal end of the cover 210 lines up substantially with boundaries of the respective compartments 208. This ensures that exactly the correct number of compartments 208 and/or items are exposed when the user accesses the drawer 204. Additionally, by ensuring that the covers 210 are retracted to precise positions, the user is able to quickly identify the correct items and correct number of items for removal without any questions of whether to remove items that are in partially exposed compartments 208, as the selected items will be the only ones that are exposed.

In operation, once the user makes a selection of one or more items to retrieve from the cabinet 100, the computing device 112 identifies one or more drawers 204 and/or compartments 208 that are associated with the selected items. The computing device 112 may then send a signal to an actuator 216 associated with the relevant compartments 208. The signal causes the relevant actuators 216 to activate to retract an attached cover 210 to expose a number of compartments 208 necessary to dispense the correct number of selected items. In some embodiments, multiple actuators 216 and covers 210 may be actuated in one session (either simultaneously or in sequence) to provide access to items in different rows and/or drawers 204. Once the relevant covers 210 have been actuated, the relevant drawers 204 may be unlocked, allowing the user to access the drawers 204 and exposed compartments 208. Once the user is done removing items, the user may close the drawer 204. Once the computing device 112 detects that the drawers 204 are closed (such as by using one or more door close sensors) the computing device 112 may lock each drawer 204 and subsequently activate the actuators 216 to extend the cover 210 over the exposed compartments 208. In such a manner, the cabinet 200 may prevent the possibility of any pinch points that may be created while the covers 210 are being moved, as the covers 210 are only moved when the drawers 204 are closed and/or locked.

In some embodiments, the actuators 216 may include one or more manual override mechanisms. Such mechanisms may allow the cover 210 to be moved manually in certain events, such as due to the occurrence of a power failure. For example, the actuator 216 may include a clutch or coupler that is disengageable from the actuator 216 to enable the user to move the cover 210 independently of the actuator 216. For example, a mechanical and/or electrical key lock may be used to enable the user to manually move the cover 210 to access the items within the compartments 208. In some embodiments, the actuator 216 may include a slot that accepts a winding key that the user may utilize to wind and/or otherwise manually manipulate the actuator 216 if access is needed and there is no power. In some embodiments, the actuator 216 may include a gearbox and/or a locking pawl that prevents the user from manually moving the cover 210 in normal operation.

Oftentimes, one or more of the compartments 208 may be empty prior to its respective cover 210 being retracted. For example, one or more users may have previously accessed a particular row of compartments 208 since the last time drawer 204 was refilled. In such embodiments, the drawer 204 may include a number of sensors that help detect whether the compartments 204, drawer 204 are empty or contain an item. Based on this information, the cover 210 may be actuated to expose a number of compartments 208 that allows access to the selected number of items. For example, if a drawer 204 includes a row of ten compartments 208 that each include a single item and a user wishes to access three items, the computing device 112 may check to see if any of the compartments 208 are empty by using one or more sensors. For example, if each of the ten compartments 208 includes an item, the computing device 112 may retract the cover 210 sufficiently far to provide access to the first three compartments 208, thereby allowing the user to remove the three items as requested. In another situation, the computing device 112 may determine that the first two compartments 208 are empty and may then retract the cover 210 sufficiently far to provide access to the first five compartments 208 (including the two empty compartments 208, thereby allowing the user to remove the three items as requested.

In some embodiments, one or of the sensors used determine whether a particular compartment 208 is full or empty may be integrated into the cover 210 itself. For example, a leading edge 230 of the cover 210 may include one or more optical sensors 232 that may be used to detect any contents of the compartments 208 as the cover 210 is retracted and/or extended. In some embodiments, the leading edge 230 may be formed from a last segment 222 of the cover 210. By placing the optical sensor 232 in the leading edge 230, the computing device 112 is able to determine whether each compartment 208 is empty as the cover 210 is retracted, starting with a distal most compartment 208 over which the cover 210 extends. In some embodiments, the optical sensors 232 (such as cameras, infrared sensors, and the like) may be configured to image the contents of a compartment 208 to determine whether one or more items are stored therein. For example, the computing device 112 may perform object detection on images captured by the optical sensor 232 of each compartment 208 as the cover 210 is extended and/or retracted. The object detection may be usable to determine whether each compartment 208 is empty or contains one or more items.

In other embodiments, the optical sensors 232 may work in conjunction with one or more features of the compartments 208 to determine whether any items are present in the compartment 208. For example, in some embodiments, a computer-readable identifier (such as a barcode, quick response (QR) code, alphanumeric text, and/or other object that is readable by a computer) may be printed, adhered, and/or otherwise placed on a bottom surface of each compartment 208. If an item is positioned within the compartment 208, the item obscures all or part of the computer-readable identifier, rendering the identifier unreadable. Thus, if the optical sensor 232 cannot read the identifier of a particular compartment 208, the computing device 112 may determine that the compartment 208 is housing an item. If the optical sensor 232 is able to read the identifier, the computing device 112 may conclude that the compartment 208 is empty.

In another embodiment, a light source, such as a light emitting diode (LED) may be provided within a base of each compartment 208. Optical sensor 232 within the leading edge 230 may be configured to detect the presence of any light emitted from the light source. In some embodiments, the optical sensor 232 may be a receiver that is configured to react to light signals that are pulsed at a particular frequency. In some embodiments, the optical sensor 232 may be in the form of a phototransitive receiver that is activated when it detects light emitted at a particular wavelength. In some embodiments, the light may include wavelengths in the IR spectrum, although other wavelengths are possible in some embodiments. If the light is detected by the optical sensor 232, the computing device 112 may determine that the compartment 208 is empty as no object is interfering with the ability of the optical sensor 232 to detect the light. Similarly, if the optical sensor 232 is unable to detect the light, the computing device may determine that the compartment 208 has an item stored therein that is blocking the light. In some embodiments, the optical sensor 232 may detect only a portion of the light emitted by the light source. In such embodiments, the computing device 112 may be programed based on the needs of a particular application. For example, in some embodiments, if the optical sensor 232 detects only a portion of the light emitted from a light source, the computing device 112 may determine that an item is blocking the rest of the light and that the compartment 208 must be occupied. In other embodiments if any light is detected the computing device 122 may determine that the compartment 208 is empty.

Figure 9:
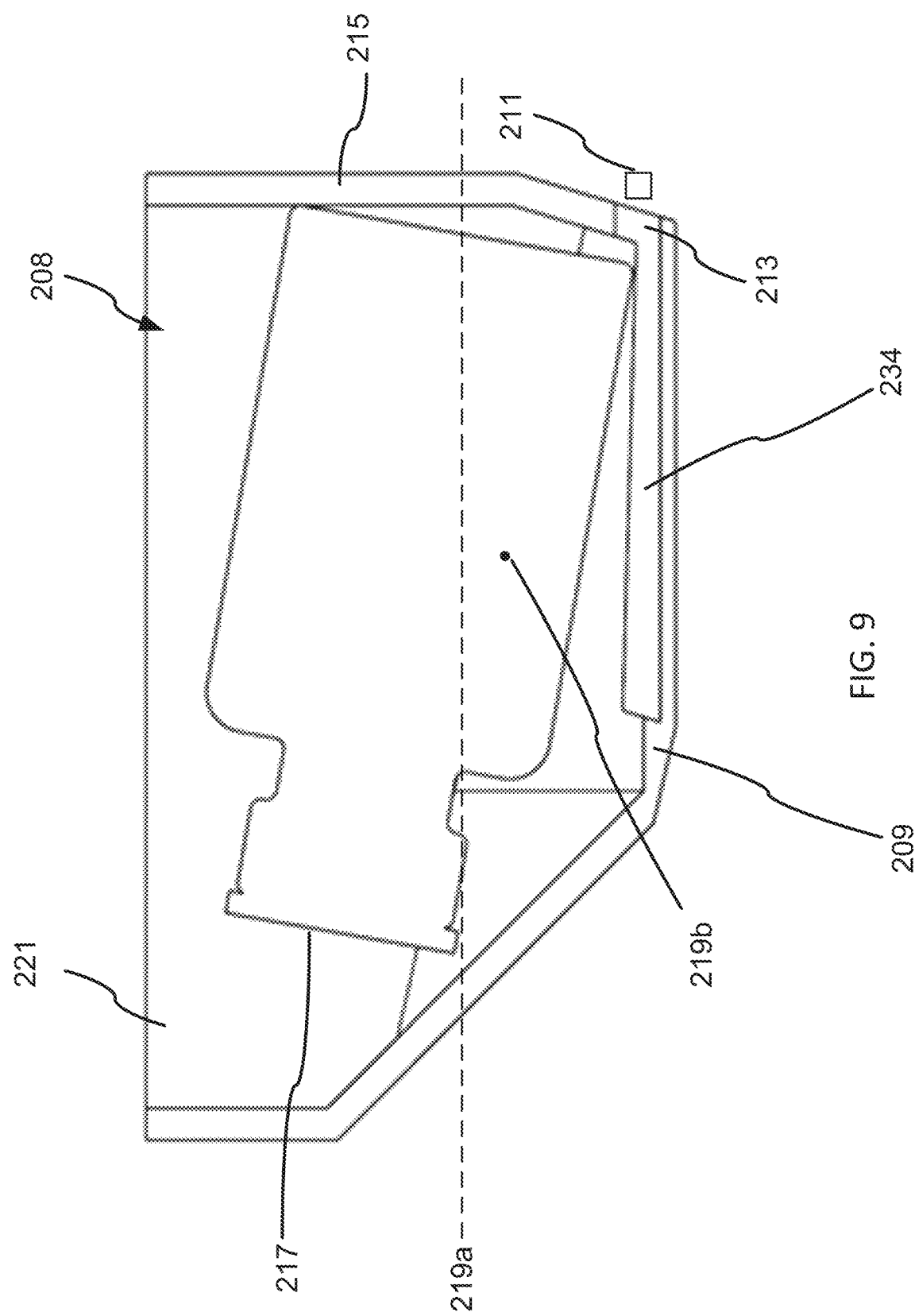
FIG. 9 illustrates a light sensor assembly of a compartment of the drawer of FIG. 4.

In some embodiments, the light source may be positioned directly in a storage area of the compartment 208, such as by placing a LED or other light source in a base 209 of the compartment 208 directly below where an item is to be stored. In other embodiments, such as that illustrated in FIG. 9, the light source 211 (such as a LED) may be positioned outside of the compartment 208. In some embodiments, such as if the compartment 208 is removable from the drawer 204) the light source 211 may be affixed to a device other than the compartment 208. For example, the light source 211 may be positioned on a housing of the drawer 204. In order to introduce the light into the interior of the compartment 208, an aperture 213 may be formed in a bottom and/or side of the compartment 208 that is in the illumination field of the light source 211. In some embodiments, a light pipe 234 and/or other structure may be provided in the base 209 of the compartment 209 to further distribute the emitted light through the compartment 208. As illustrated, the light pipe 234 may be coupled with a portion of the base 209 of the compartment 208 and extends through a sidewall 215 of the compartment 208, serving to direct light from an externally located light source 211 to be introduced into the interior of the compartment 208. Oftentimes, the light pipe 234 is positioned in a central region of the compartment 208, which may help ensure that if an item is present within the compartment 208 then the light and light pipe 234 will be obstructed from detection by the optical sensor 232.

In some embodiments, the compartment 208 and/or light pipe 234 may be designed to further ensure that items present within the compartment 208 will obstruct the light from being detected by the optical sensor 232. For example, as illustrated, the light pipe 234 may only extend along a portion of the length of the compartment 208, such that no portion of the light pipe 234 extends beyond a distal end 217 of an item placed within the compartment 208. Additionally, the base 209 of each compartment 208 may be sloped along one or more axes 219a. 219b toward the light pipe 234, thereby biasing items stored within the compartment 208 to be positioned directly above the light pipe 234 in order to obstruct the light emitted from the light pipe 234. For example, lateral sides 221 of the base of each compartment 208 may be curved and/or otherwise tapered toward light pipe 234 positioned in the center of the compartment 208. Additionally, the base 209 of each compartment 208 may be sloped from one longitudinal end opposite the light source toward the other longitudinal end through which the light source 211 and light pipe 234 extend. Not only does the tilting of the base 209 of the compartments 208 help ensure that items placed within the compartment 208 are positioned to cover the light pipe 234 to increase the accuracy of optical sensors 232, but also helps to make items easier to remove from the compartments 208.

In some embodiments, non-optical sensors may be used instead of or in conjunction with optical sensors to determine whether a particular compartment 208 is empty. For example, each compartment 208 may include one or more load sensors positioned in or below a base of the compartment 208. These load sensors (such as strain gauges, capacitive sensors, and the like) may be calibrated to provide non-zero readings when an item is present. In some embodiments, a measurement of a load sensor may be compared to a known weight of a particular item that is expected to be stored in a given compartment 208. If the load measurement matches the known weight within an error factor of the load sensor, the computing device 112 may determine that the compartment 208 associated with the load sensor is housing an item.

In another embodiment, each item within a compartment 208 may include an RF tag (passive or active) that may be read by an antenna disposed on the leading edge 230 of the cover 210 as the cover 210 is extended and/or retracted. In such embodiments, RF shielding may be provided on the walls and base of each compartment 208 such that only items within a single compartment 208 may be read at a single time by the antenna. It will be appreciated hat other sensors may be integrated into the cover 210, compartment 208, and/or drawer 204 to track the presence and usage of items positioned within the compartments 208.

In addition to helping determine the filled status of a compartment 208 to actuate the cover 210 a correct distance, the information from sensors may be used to help monitor an inventory of the drawer 204. For example, after the cover 210 is retracted and/or extended, the computing device 112 may monitor how many compartments 208 have items stored therein based on data from the various sensors. This information may be tracked, oftentimes along with information about which users took the items and possibly for what purpose (task, patient, etc.) to monitor how many items are present within the drawer 204 and/or cabinet 100 and how items have been utilized. In some embodiments, the inventory and/or usage data may be updated each time the covers 210 are extended and/or retracted and/or when each drawer 204 is opened and/or closed.

Figure 11:
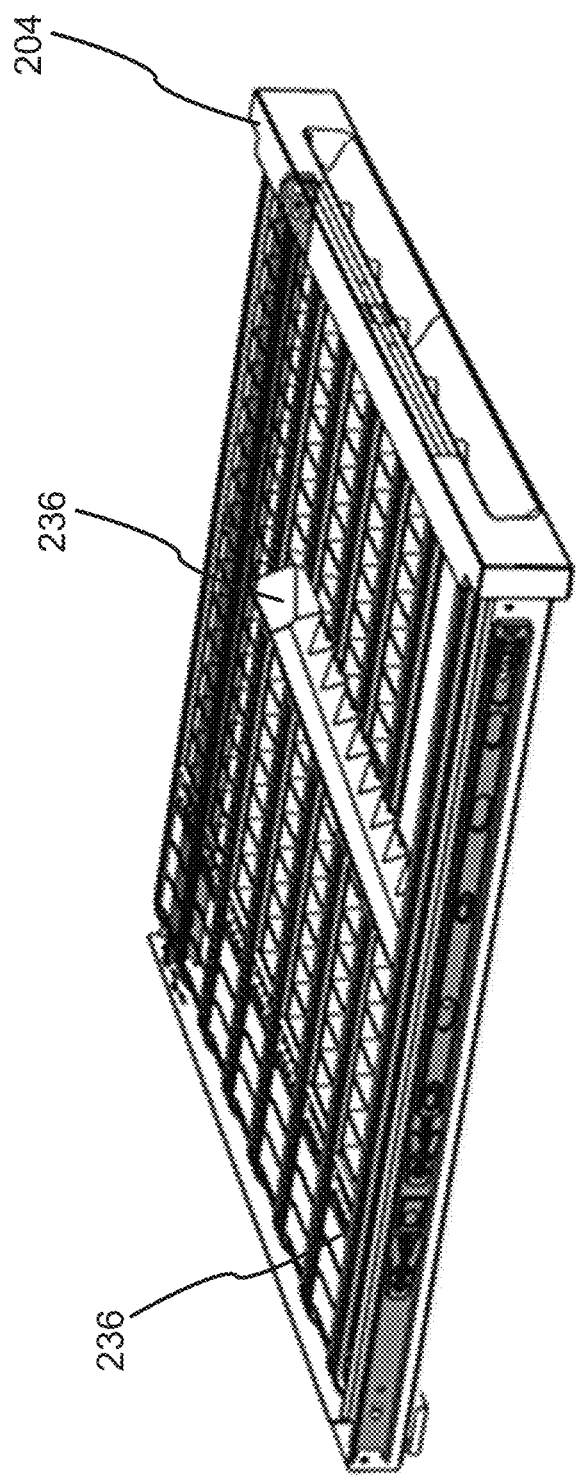
FIG. 11 illustrates a cassette that forms a portion of a row of compartments according to embodiments of the invention.

In some embodiments, compartments may be formed as part of the drawers 204 themselves. In other embodiments, such as illustrated here, the compartments 208 may be separately formed and subsequently coupled with a base of the drawers 204. For example, each compartment 208 may be formed as an individual bin that is later coupled with a base of the drawer 204. In other embodiments, such as that shown in FIGS. 10A and 10B, each compartment may be formed as part of a cassette 236 and/or other removable feature that includes a number of compartments 208. While illustrated with ten uniformly sized compartments 208, it will be appreciated that cassette 236 may include any number and size of compartments 208. Additionally, while arranged in a single row, it will be appreciated that in some embodiments a cassette 236 may include multiple rows of compartments 208. In some embodiments, each cassette 236 may form an entire row of compartments 208 within a drawer 204. In other embodiments, a cassette 236 may form only a portion of a row of compartments 208, such as one half or other fraction of a row of compartments 208. Such a configuration provides benefits associated with refilling the drawer 204. For example, if the compartments 208 in a given row are divided into two cassettes 236 as shown in FIG. 11, a refill alert may be generated when the first half of the row is empty, ensuring that the refill occurs while the second half of the row is still has items available to a user. To refill the first half, the user may use the computing device 112 to select a refill procedure. This may cause the computing device 122 to retract the cover 210 to expose at least the first half of the row so that the empty one of the cassettes 236 may be removed and replaced with a full cassette 236. In other embodiments, a drawer 204 may be refilled on a compartment by compartment basis. In such embodiments, the cover 210 may be retracted to expose all empty compartments 208 and a user and/or pick and place robot may insert the correct items into the empty compartments 208. In some embodiments, the cassettes 236 may include covers (not shown) for transporting full cassettes 236. For example, once a cassette 236 has been filled by a pharmacy, a cover (such as a reusable cover, a cover similar to cover 110, a one-time use cover (such as a tape or other film), and/or other cover) may be positioned atop the various compartments 208 within the cassette 236. Before, during, and/or after the cassette 236 is inserted into a drawer 204, the cover may be removed such that the cover 210 of the drawer 204 may be used to control access to the various items within the compartments 208.

As illustrated, each compartment 208 within the cassette 236 may include light pipe 234. The light sources may be coupled with the compartments 208 and/or disposed within the drawer 204 such that when the cassette 236 is mounted within the drawer 204 the light sources are in alignment with the light pipes 234 of the individual compartments 208. In some embodiments, other sensors, such as load sensors, RF sensors, and the like may be coupled with the cassette 236 and/or with the drawer 204 itself. In some embodiments, each cassette 236 may include an identifier (such as an identifier that is encoded onto an RF chip) that indicate which items and/or drawer 204 are associated with the given cassette 236.

Figure 12:
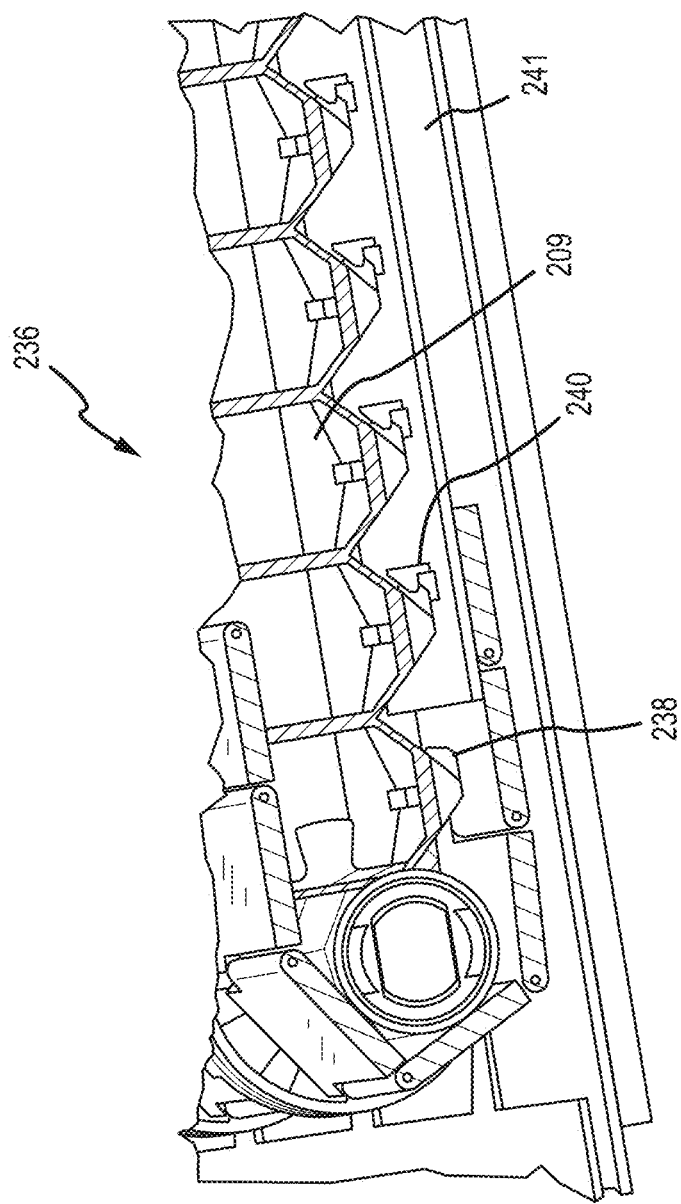
FIG. 12 illustrates a mating assembly for mounting a cassette within a drawer according to embodiments of the invention.

In some embodiments, each cassette 236 may include the cover 210 and actuator 216 assembly, while in other embodiments, the cassettes 236 may be inserted into the cover 210 and actuator 216 assembly. For example, the cover 210 and actuator 216 assembly may be coupled with the drawer 204 such that to insert a cassette 236 the cover 210 must be at least partially retracted. In some embodiments, an underside of each of the cassettes 236 may include one or more mating features, such as clips 238, buttons, magnets, and/or other coupling mechanisms that are configured to secure the cassette 236 to the base 241 of the drawer 204. As illustrated in FIG. 12, the base 241 of the drawer 204 may define one or more mating features 240 (such as recesses and/or other structures that may serve as mounting locations) that are configured to engage with the clips 238 and retain the cassette 236 within the drawer 204. In some embodiments, the connection of mating features (such as the engagement of clips 238 into the mating features 240) of the cassettes 236 and the drawers 204 may be similar to those in ski boots, where a front end of a connector is inserted into a mating feature and the rear end is forced downward to lock the cassette 236 in place.

Figure 13:
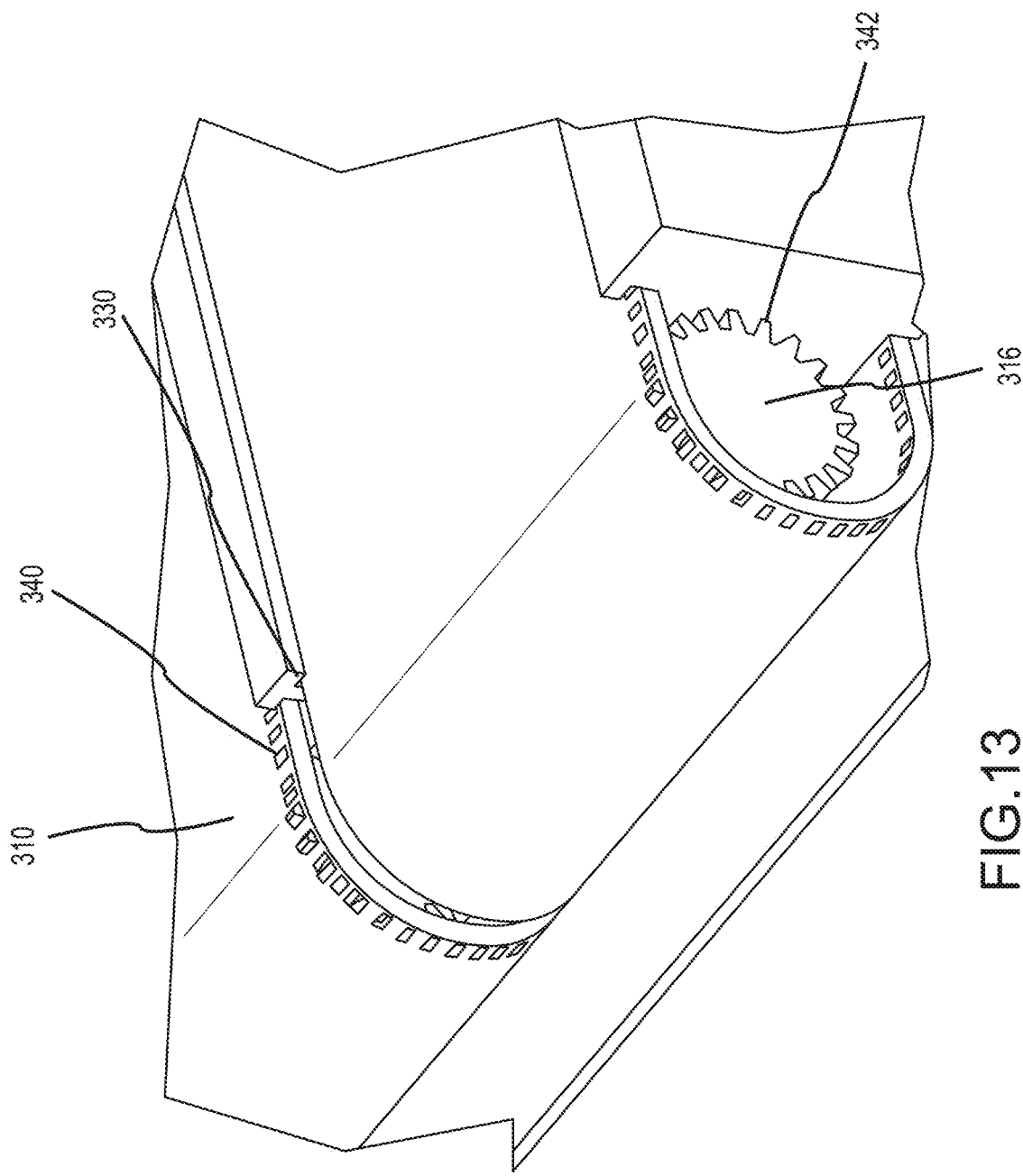
FIG. 13 illustrates an alternative embodiment of a cover according to embodiments.

FIG. 13 illustrates an alternative embodiment of a cover 310. Cover 310 may operate in a manner similar to cover 210 described above. Here, cover 310 is a formed of a single piece of flexible material (such as sheet metal, polymers, and the like) that is capable of being curved about an actuator and/or drive component coupled with the actuator (such as gear 316) as the cover is retracted and/or extended. Lateral edges of cover 310 define a number of apertures 340 that are configured to receive cogs 342 of the actuator 316, allowing the actuator 316 to propel the cover 310. In some embodiments, the motion of cover 310 is constrained by a track 330 formed above and/or below individual compartments of a drawer.

Figure 14:
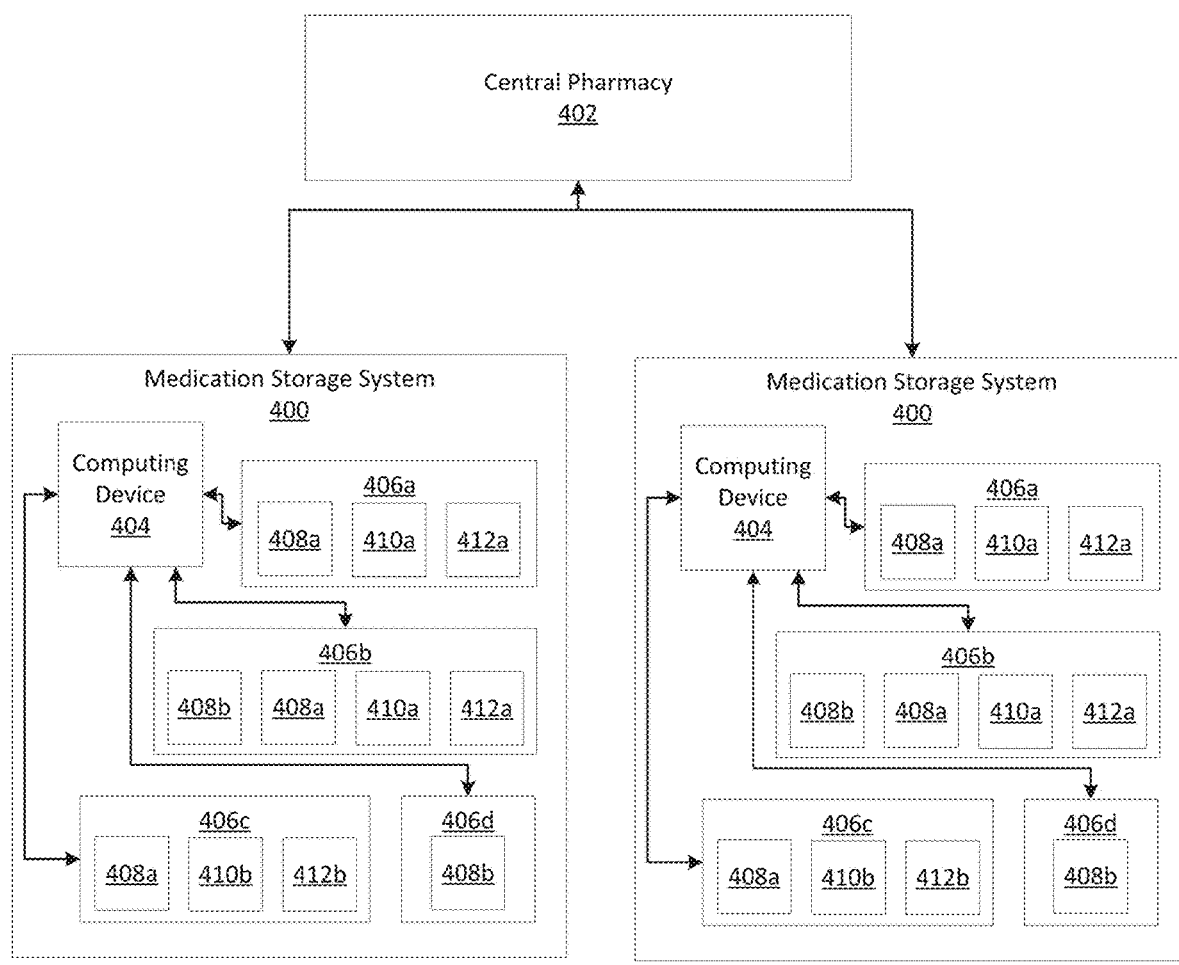
FIG. 14 is a block diagram of a medication control system according to embodiments.

FIG. 14 illustrates an embodiment of a medication control system 414. In one particular embodiment, a medication control system 414 may be provided in a medical facility, such as a hospital or clinic. In such embodiments, the medication control system 414 may include one or more medication storage systems 400 that are in communication with a central computing device, such as a central pharmacy 402. Each medication storage system 400 may be embodied in any form, such as a cabinet (similar to cabinet 100), cart, shelf, locker, and/or other storage unit and may be positioned in a particular room, floor, and/or ward of the facility.

Each medication storage system 400 may include a computing device 404 (similar to computing device 112) that is configured to communicate information between the medication storage system 400 and the central pharmacy, authenticate users of the medication storage system 400, and control access to medications and/or other items stored within the medication storage system 400. The computing device 404 may include and/or be communicatively coupled with a display screen and at least one input device, such as a keyboard, mouse, touchscreen, credential reader, microphone, camera and/or other device that enables a user to interact with the computing device 404. The credential reader may be in the form of a wireless reader, such as a Bluetooth, RFID. NFC, and/or other wireless reader that may read information from an active or passive user credential, such as a fob, mobile phone, ID, and/or other credential device. In other embodiments, the credential reader may include a contact reader, such as a chip or magnetic stripe reader. In yet other embodiments, the credential reader may include a biometric reader, such as a camera or other optical sensor for facial, iris, and/or palm vein authentication, a microphone for voice authentication, a fingerprint reader, and/or other biometric sensor.

A user is able to interact with the computing device 404 using one or more of the input devices to log in, select a patient and/or procedure, and/or gain access to items stored within the mediation storage system 400. For example, to log in to the mediation storage system 400, the user may enter a user name, password, and/or other access credential (which may include a biometric credential) to verify that the user is authorized to access the cabinet 100 and/or a particular item stored therein. In other embodiments, a user may be logged in automatically if a wireless credential of the user is brought within range of a wireless credential reader of the computing device 404. Once a user is logged in, the user may make selections about a patient, procedure, and/or items to be removed or otherwise dispensed from the medication storage system 400. These selections may be made using any of the input devices of the computing device 112. In one typical basic medical usage scenario, a health care worker may enter an identification of a patient who is under the care of the health care worker, and who will need medication during the worker's current rounds. Computing device 404 may access the patient's medical file and determine what medications have been prescribed for that patient. In other embodiments, a user may merely select one or more items to remove from the medication storage system 400, without the need to compare the data to an order, such as a patient treatment plan.

Once the user has selected which items are to be removed, the medication storage system 400 may provide access to the items, such as by the computing device 404 unlocking one or more drawers 406 (similar to drawers 104 and 204 as described above) that are configured to store various medications and/or other items. Before, during, and/or after the user has removed any items from the cabinet 100, the computing device 404 and/or other computer system may use any number of sensors to monitor which items were actually removed from the medication storage system 400. The drawers 406 may be independently lockable such that access to each drawer 406 may be controlled individually. In some embodiments, a mediation storage system 400 may include drawers 406 of a single configuration. In other embodiments, such as illustrated here, the medication storage system 400 may include drawers 406 of different layouts and/or sizes.

For example, as illustrated, the medication storage system 400 includes four drawers 406 that each have a different size and/or drawer layout, although it will be appreciated that any number of combinations of drawer sizes and/or layouts is possible in some embodiments. Here, drawer 406a defines a storage region that has been separated into a number of bins and/or other compartments 408a for receiving one or more items. The compartments 408a may be arranged in rows and/or columns within the interior of the drawer 406a. Compartments 408a are configured to be covered by a retractable and/or otherwise removable cover 410a. Cover 410a may be similar to covers 210 and 310 described above. For example, a number of covers 410a are provided that extend across an entire row of compartments 408a, which may be oriented across a width of the drawer 406a. Oftentimes, covers 410a extend across the entire row of compartments 408a. In other embodiments, one or more covers 410a may extend across any portion of a row of compartments 408a. Each cover 410a may be configured to be retracted to expose a selected number of compartments 408a and/or items. The cover 410a encloses the compartment 408a such that any item present within the compartment 408a may not be accessible to permit retrieval of the item. The cover 410a is moveable using an actuator 412a (similar to actuator 116 and 216 described above) that moves the cover 410a to uncover an item stored within the compartment 408a. For example, the actuator 412a may be coupled with each of the covers 410a such that the covers 410a may each be actuated to extend and/or retract the covers 410a independently of one another.

In one example, each of the one or more compartments 408a may be uncovered in a sequence, such that all compartments 108 that have been previously uncovered remain uncovered. In another example, the cover 410a may allow only one compartment 408a to be uncovered at any given time and for the rest of the compartments 408a associated with that cover 410a to be enclosed by the cover 410a. This ensures that if a user wants an item in a particular row of compartments 408a, only items from that row are exposed when the user accesses the drawer 406a. In addition to controlling access to non-selected items, by retracting covers 410a of only compartments 408a and/or items that are selected by the user prior to access, the user is able to quickly identify the items for removal, as the selected items will be the only ones that are not covered.

As illustrated, medication storage system 400 includes another drawer 406b. Here, drawer 406b includes both covered compartments 408a and open-topped compartments 408b. Covered compartments 408a include covers 410a and actuators 412a to control access to items within a row of covered compartments 408a. The open-topped compartments 408b may be disposed within the drawer 406b in any arrangement. Oftentimes, open-topped compartments 408b are used to store non-controlled substances and/or other items that do not require the additional security of a covered compartment 408a. To provide access to an item in an open-topped compartment 408b, the computing device 404 merely needs to unlock the relevant drawer 406b.

Medication storage system 400 also includes a drawer 406c that includes covered compartments 408a. Here, columns of the covered compartments 408a have corresponding covers 410b and actuators 412b. Covers 410b and actuators 412b operate similarly to covers 410a and actuators 412a, however the covers 410b are arranged over columns of compartments 408a and the actuators 412b retract and extend the covers 410b along a length of the drawer 406c, rather than the width of the drawer 406c. Medication storage system 400 also includes a drawer 406d that includes only open-topped compartments 408b. It will be appreciated that the arrangement of various drawers 406, compartments 408, covers 410, and actuators 412 provided above is merely meant to serve as one example, and that numerous variations are possible.

In embodiments, once the user makes his selection of one or more items to retrieve from the medication storage system 400, the computing device 404 identifies one or more drawers 406 and/or compartments 408 that are associated with the selected items. The computing device 404 may then send a signal to an actuator 412 associated with the relevant compartments 408. The signal causes the relevant actuators 412 to activate to retract an attached cover 410 to expose a number of compartments 408 necessary to dispense the correct number of selected items. In some embodiments, multiple actuators 416 and covers 410 may be actuated in one session (either simultaneously or in sequence) to provide access to items in different rows and/or drawers 406. Once the relevant covers 410 have been actuated, the relevant drawers 406 may be unlocked, allowing the user to access the drawers 406 and exposed compartments 408. Once the user is done removing items, the user may close the drawer 406. Once the computing device 112 detects that the drawers 104 are closed (such as by using one or more door close sensors), the computing device 404 may lock each drawer 406 and subsequently activate the actuators 412 to extend the cover 410 over the exposed compartments 408. In such a manner, the medication storage system 400 may prevent the possibility of any pinch points that may be created while the covers 410 are being moved, as the covers 410 are only moved when the drawers 406 are closed and/or locked.

In some embodiments, the drawer 406 and/or cover 410 may include a number of sensors that are used to monitor inventory within the drawer 406 and/or whether a compartment 408 is full or empty. For example, as described in greater detail above, each compartment 408 of the drawer 406 may include a light, image, RF, and/or weight-based sensor that determines whether the compartment 408 includes an item. Similarly, a leading edge of each cover 410 may include a light, image, and/or RF-based sensor that is used to determine whether a given compartment is empty or full. In some embodiments, when the medication storage system 400 is idle, each cover 410 may be fully retracted to count the items within each drawer 406. In other embodiments, a running inventory may be maintained based on a log of interactions with the medication storage system 400. Based on knowledge of whether each compartment 408 is empty or full, the inventory of a drawer 406 may be determined. This inventory information may be tracked, oftentimes along with information about which users took the items and possibly for what purpose (task, patient, etc.) to monitor how many items are present within the drawer 406 and/or medication storage system 400 and how items have been utilized. In some embodiments, the inventory and/or usage data may be updated each time the covers 410 are extended and/or retracted and/or when each drawer 406 is opened and/or closed.

In some embodiments, the inventory may be updated periodically, such as every hour, work shift, day, etc. In other embodiments, the inventory may be tracked continuously before, during, and/or each interaction with the medication storage system 400. In some instances, the central pharmacy 402 may initiate a remote inventory scan of one or more of the medication storage systems 400 in the facility. For example, the central pharmacy 402 may send a command to each medication storage system 400 that causes the latest inventory information from the respective medication storage system 400 to be sent to the central pharmacy. In some instances, the command may cause each medication storage system 400 to actuate sensors and/or covers 410 to determine a current inventory count, such as by fully retracting and/or extending each cover 410 to count the various items. This inventory information may be transmitted to the central pharmacy 402. The central pharmacy may monitor the inventory of each medication storage system 400 and use the information to determine when to refill a particular item in a particular drawer 406 and/or medication storage system 400. Additionally, such information may be useful in determining when to reorder a particular item, as the facility-wide inventory may be known based on the inventory of each medication storage system 400 and of the central pharmacy.

In some embodiments, the knowledge of the empty/full state of each compartment 408 enables the cover 410 to be actuated to expose a number of compartments 408 that allows access to the selected number of items. For example, if a drawer 406 includes ten single-item compartments 408 covered by a single cover 410, the computing device 404 may check to see if any of the compartments 408 are empty by using one or more sensors. For example, if each of the ten compartments 408 includes an item, the computing device 404 may retract the cover 410 sufficiently far to provide access to the first three compartments 408, thereby allowing the user to remove the three items as requested. In another situation, the computing device 404 may determine that the first two compartments 408 are empty and may then retract the cover 410 sufficiently far to provide access to the first five compartments 408 (including the two empty compartments 408), thereby allowing the user to remove the three items as requested.

Figure 15:
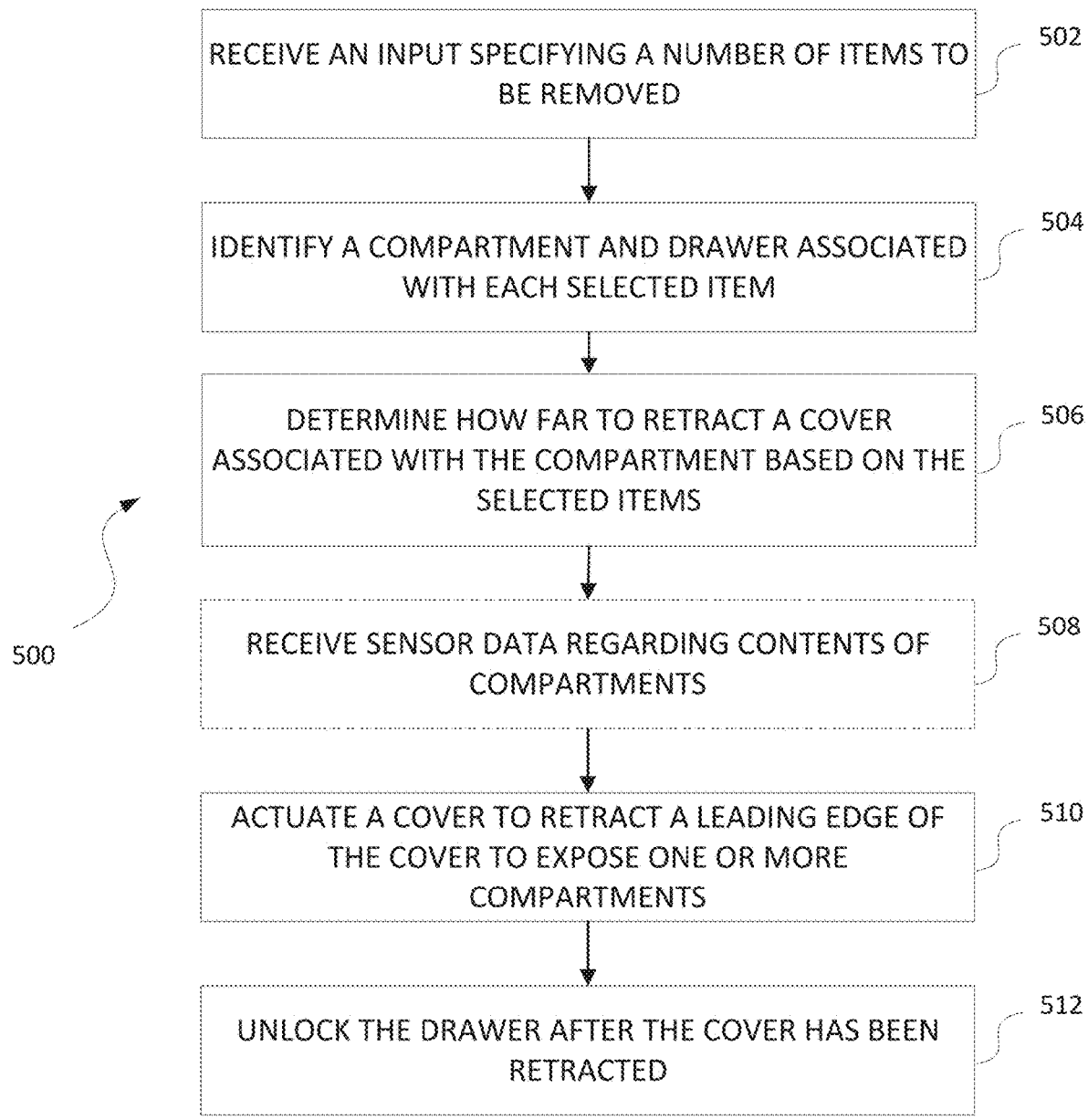
FIG. 15 is a flowchart depicting a process for operating a secure dispensing mechanism according to embodiments.

FIG. 15 is a flowchart illustrating a process 500 of operating a secure dispensing mechanism. The secure dispensing mechanism may be integrated into a storage unit, such as cabinet 100, medication storage system 400, a cart, shelving, and/or other device that may include a number of secure dispensing units (such as drawers 104, 204). The secure dispensing mechanism may include one or more processors or other controllers (such as computing devices 112, 404) that execute instructions to perform some or all of the steps of process 500. At block 502, an input may be received to dispense a selected number of items from a secure dispensing mechanism. The input may specify which items are to be removed and how many items are to be removed. The input may be received by a computing device, and oftentimes may be received from an authorized user. The authorized user may have previously been authenticated by providing some sort of access credentials to the computing device, such as a piece of information, an identifier from a possession-based credential, and/or a biometric credential. In some embodiments, the authenticated user may be required to entire additional information associated with a particular item, such as a patient and/or task that the item is to be used with.

After any user authentication has been performed and item selections have been received, the secure dispensing mechanism may identify one or more compartments and/or drawers within the storage unit that contain the selected items at block 504. For example, the computing device may access a local and/or remote database of items (such as medications) and drawer/compartment locations. In some embodiments, each drawer, cassette, and/or bin may include a computer readable identifier that informs the computing device what drawer/item arrangements are present. Once the computing device identifies a proper drawer and/or compartment that contains the selected item(s), the computing device may determine how much a cover associated with the relevant compartment needs to be retracted at block 506.

In some embodiments, the cover may be extended to cover all compartments, including empty compartments, after each interaction. In such embodiments, the computing device may receive sensor data that is used to determine how much to retract the cover to expose the selected items at block 508. For example, if each compartment includes a single item and there are no empty compartments, the cover may be retracted to expose a number of compartments matching the number of items selected. In other embodiments, the number of compartments may not match the number of items selected. For example, one or more of the compartments may include multiple items. In other embodiments, the secure dispensing mechanism may determine that at least one of the plurality of compartments is empty and adjust the selected number of the plurality of compartments to expose based on the determination that the at least one of the plurality of compartments is empty. For example, a row of ten compartments each includes a single item and a user wishes to access three items in the row, the secure dispensing unit may check to see if any of the compartments are empty by using one or more sensors, such as optical sensors, radio frequency (RF) sensors, load sensors, and the like. For example, if each of the ten compartments includes an item, the secure dispensing mechanism may retract the cover sufficiently far to provide access to the first three compartments, thereby allowing the user to remove the three items as requested. In another situation, the secure dispensing mechanism may determine that the first two compartments are empty and may then retract the cover sufficiently far to provide access to the first five compartments (including the two empty compartments), thereby allowing the user to remove the three items as requested. Once the proper retraction distance is determined, the computing device may send a command to an actuator associated with the compartment to actuate a cover to retract a leading edge of the cover to expose a selected number of compartments at block 510.

In determining that at least one of the plurality of compartments is empty, the secure dispensing mechanism may detect an optical signal from one or more emitter devices positioned within the at least one of the plurality of compartments. In some embodiments, an optical sensor positioned on the leading edge of the cover as the cover is moved along a length of the secure dispensing mechanism to detect the optical sensor. In other embodiments, imaging sensors, weight sensors, and/or RF sensors may be integrated into the cover and/or compartments to assist the computing device in determining whether a particular bin is empty.

In other embodiments, once the cover is partially retracted, the cover will remain in place until another interaction with the associated row of compartments (such as another selection to remove an item and/or refilling the empty items), thereby keeping empty containers exposed. In such embodiments, no sensor data is needed and the cover may be actuated to expose a number of compartments matching the number of items at block 510.

In some embodiments, multiple covers may be actuated and/or multiple rows of compartments may be exposed. In embodiments in which multiple covers (in the same row and/or different rows) are actuated, the covers may be actuated in sequence and/or simultaneously to provide access to all selected items at once. In some embodiments, actuating the cover may include rotating a sprocket gear drive that is interfaced with an edge of the cover to pull at least a portion of the cover about a portion of the sprocket gear drive.

In some embodiments, the cover and compartments may be integrated into an electronically lockable drawer of an inventory control system (such as cabinet 100 and/or medication storage system 400). In such embodiments, the process 400 may further include unlocking the lockable drawer after the cover of the secure dispensing mechanism has been retracted at block 512. The user then has access to the interior of the drawer and the exposed compartments. After the user has removed the desired items, the drawer is shut. Once the computing device detects that a drawer has been shut, the computing device may send a command that locks the drawer, while in other embodiments the drawer may have a self-locking mechanical lock. Once, the drawer has been locked, in some embodiments, the computing device may optionally extend the cover over each of the compartments. In some embodiments, the secure dispensing mechanism may receive an additional input to refill at least some of the compartments. The cover may be retracted to expose a number of compartments that are to be refilled, which may include all of the compartments or only a portion thereof.

In some embodiments, the process 500 may also include scanning each of the compartments while the dispensing mechanism is closed and idle to determine the contents of the dispensing mechanism. For example, each of the covers within a given drawer may be actuated (in sequence, in groups, or all covers simultaneously) such that the various sensors may detect the contents of each compartment for inventory purposes. In such a manner, the contents of each drawer and/or cabinet may be captured while the cabinet is not being used. In some embodiments, the results of the inventory check may be sent to a central server and/or other remote computer, which may allow for various processes, such as refilling cassettes and/or drawers and/or reordering items to be triggered. In some embodiments, such inventory procedures may be done at predetermined times and/or intervals, after a particular use of the cabinet and/or drawer, and/or based on a request from a remote computing device (such as a central server and/or pharmacy computer).

Figure 16:
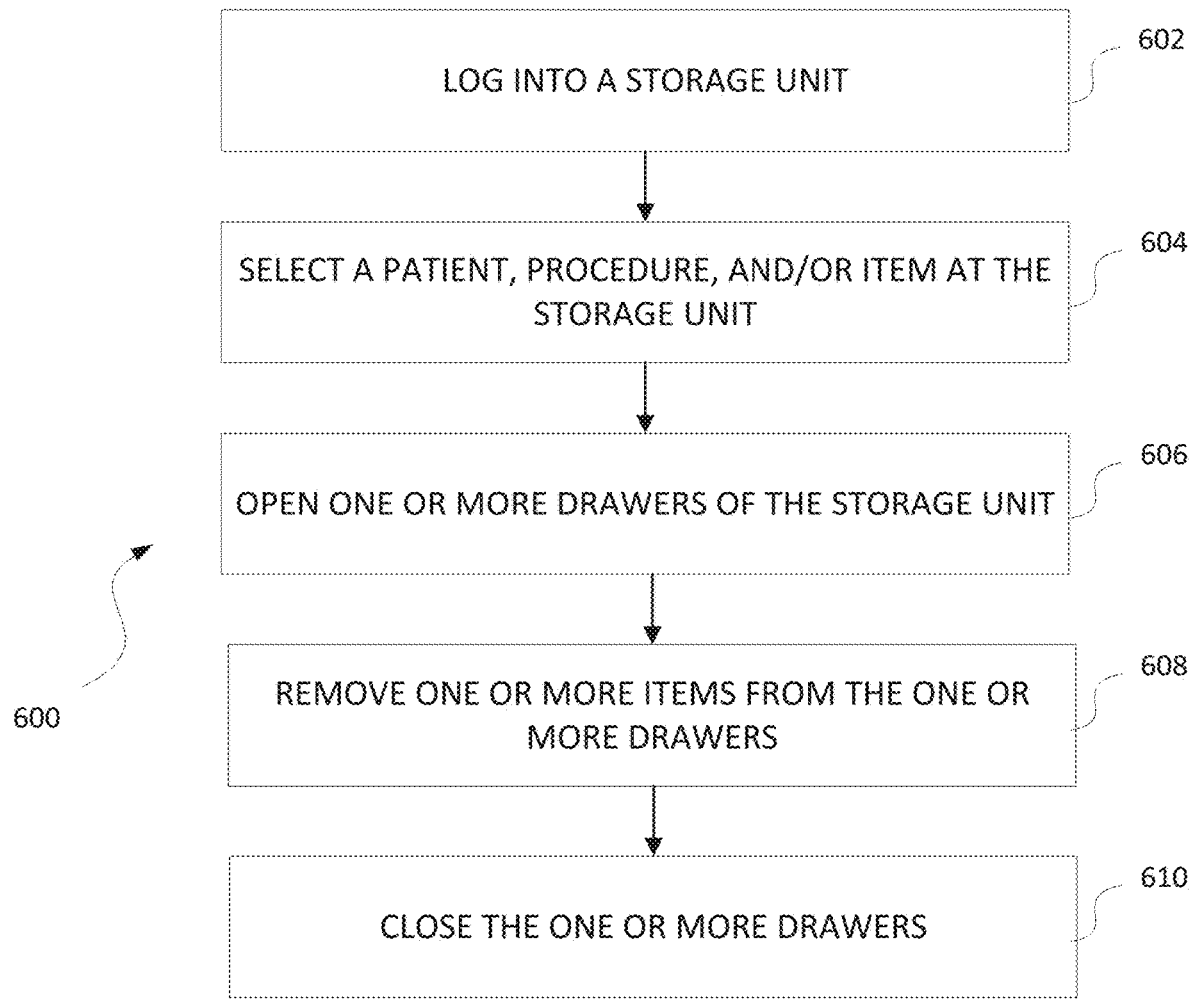
FIG. 16 is a flowchart depicting a process for using a secure dispensing mechanism according to embodiments of the present invention.

FIG. 16 is a flowchart illustrating a process 600 for using a secure dispensing mechanism. The secure dispensing mechanism may be integrated into a storage unit, such as cabinet 100, medication storage system 400, a cart, shelving, and/or other device that may include a number of secure dispensing units (such as drawers 104, 204). Process 600 may begin at block 602 by a user logging into the storage unit. For example, the user may use one or more input devices of a computing device of the storage unit to provide knowledge-based, biometric, and/or possession-based credentials as described in greater detail in relation to FIG. 1 above. Once authenticated, the user may then select use a graphical user interface (GUI) and/or other interface of the storage unit to make selections about a patient, procedure, and/or items to be removed or otherwise dispensed from the storage unit at block 604. These selections may be made using any of the input devices of the computing device, including a microphone to enable voice commands. After selections are made, the user may open one or more drawers of the storage unit that have been unlocked by the computing system at block 606. The user may then remove and/or otherwise access any items that are provided in exposed compartments within the open drawer at block 608. For example, a cover of one or more of the compartments may have been retracted by the computing device prior to the user opening the drawer. The user may then take items from the exposed compartments. In some embodiments, lights and/or other indicators may be illuminated and/or otherwise activated to guide the user to the compartment(s) containing the selected items. Once the user has all of the selected items from a given drawer, the user may close the drawer at block 610, which may then be locked by the computing device.

Figure 17:
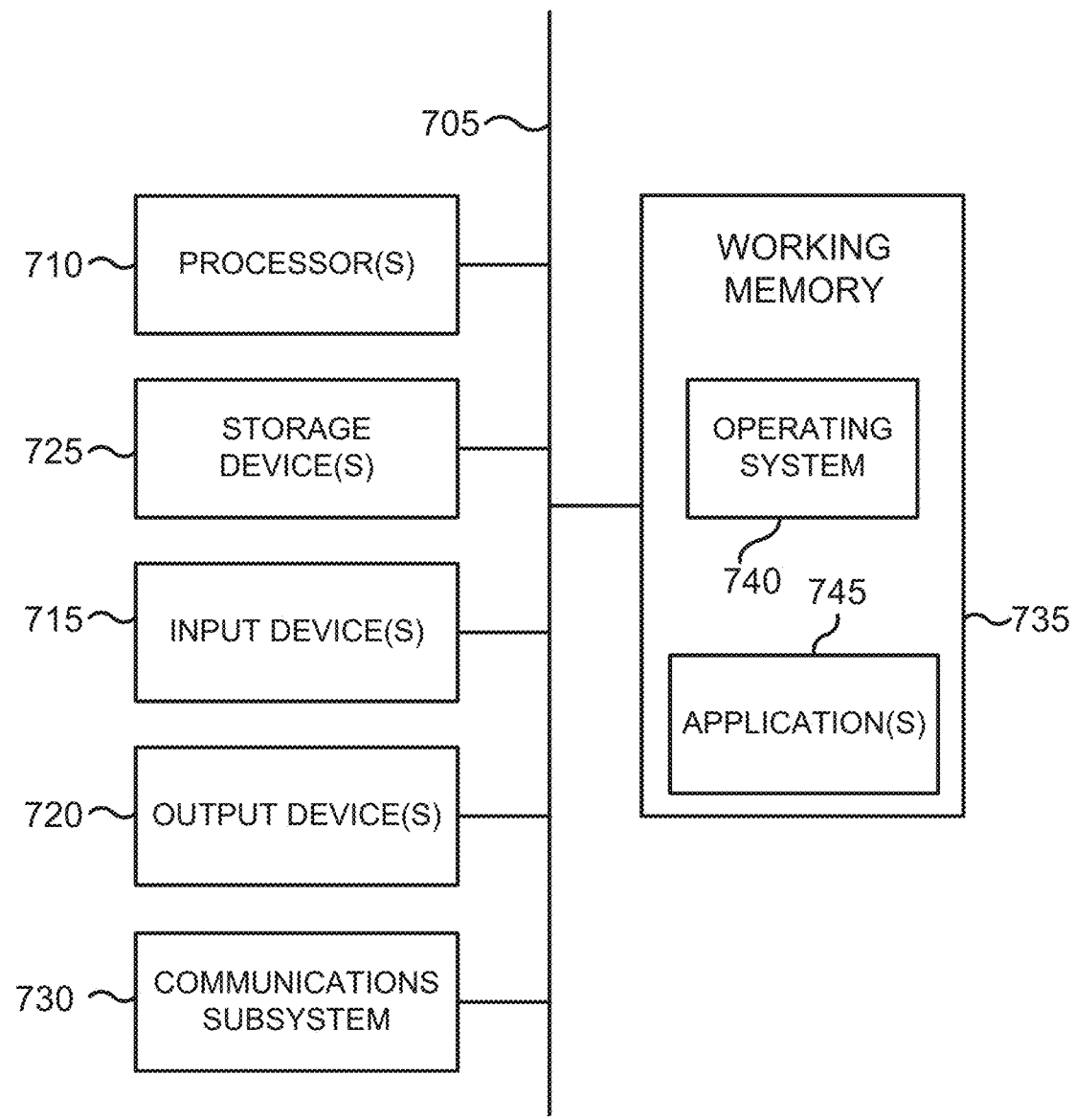
FIG. 17 is a block diagram of a computing device in accordance with embodiments of the present invention.

A computer system as illustrated in FIG. 17 may be incorporated as part of the previously described computerized devices. For example, computer system 700 can represent some of the components of computing device 112, cabinet 100, and/or other computing devices described herein. FIG. 17 provides a schematic illustration of one embodiment of a computer system 700 that can perform the methods provided by various other embodiments, as described herein. FIG. 17 is meant only to provide a generalized illustration of various components, any or all of which may be utilized as appropriate. FIG. 17, therefore, broadly illustrates how individual system elements may be implemented in a relatively separated or relatively more integrated manner. The computer system 700 is shown comprising hardware elements that can be electrically coupled via a bus 705 (or may otherwise be in communication, as appropriate). The hardware elements may include a processing unit 710, including without limitation one or more processors, such as one or more special-purpose processors (such as digital signal processing chips, graphics acceleration processors, and/or the like); one or more input devices 715, which can include without limitation a keyboard, a touchscreen, receiver, a motion sensor, a camera, a smartcard reader, a contactless media reader, and/or the like; and one or more output devices 720, which can include without limitation a display device, a speaker, a printer, a writing module, and/or the like.

The computer system 700 may further include (and/or be in communication with) one or more non-transitory storage devices 725, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 700 might also include a communication interface 730, which can include without limitation a modem, a network card (wireless or wired), an infrared communication device, a wireless communication device and/or chipset (such as a Bluetooth™ device, an 502.11 device, a Wi-Fi device, a WiMAX device, an NFC device, cellular communication facilities, etc.), and/or similar communication interfaces. The communication interface 730 may permit data to be exchanged with a network (such as the network described below, to name one example), other computer systems, and/or any other devices described herein. In many embodiments, the computer system 700 will further comprise a non-transitory working memory 735, which can include a RAM or ROM device, as described above.

The computer system 700 also can comprise software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such special/specific purpose code and/or instructions can be used to configure and/or adapt a computing device to a special purpose computer that is configured to perform one or more operations in accordance with the described methods.

A set of these instructions and/or code might be stored on a computer-readable storage medium, such as the storage device(s) 725 described above. In some cases, the storage medium might be incorporated within a computer system, such as computer system 700. In other embodiments, the storage medium might be separate from a computer system (e.g., a removable medium, such as a compact disc), and/or provided in an installation package, such that the storage medium can be used to program, configure and/or adapt a special purpose computer with the instructions/code stored thereon. These instructions might take the form of executable code, which is executable by the computer system 700 and/or might take the form of source and/or installable code, which, upon compilation and/or installation on the computer system 700 (e.g., using any of a variety of available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system. For example, a risk management engine configured to provide some or all of the features described herein relating to the risk profiling and/or distribution can comprise hardware and/or software that is specialized (e.g., an application-specific integrated circuit (ASIC), a software method, etc.) or generic (e.g., processing unit 710, applications 745, etc.) Further, connection to other computing devices such as network input/output devices may be employed.

Some embodiments may employ a computer system (such as the computer system 700) to perform methods in accordance with the disclosure. For example, some or all of the procedures of the described methods may be performed by the computer system 700 in response to processing unit 710 executing one or more sequences of one or more instructions (which might be incorporated into the operating system 740 and/or other code, such as an application program 745) contained in the working memory 735. Such instructions may be read into the working memory 735 from another computer-readable medium, such as one or more of the storage device(s) 725. Merely by way of example, execution of the sequences of instructions contained in the working memory 735 might cause the processing unit 710 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 700, various computer-readable media might be involved in providing instructions/code to processing unit 710 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 725. Volatile media include, without limitation, dynamic memory, such as the working memory 735. Transmission media include, without limitation, coaxial cables, copper wire, and fiber optics, including the wires that comprise the bus 705, as well as the various components of the communication interface 730 (and/or the media by which the communication interface 730 provides communication with other devices). Hence, transmission media can also take the form of waves (including without limitation radio, acoustic and/or light waves, such as those generated during radio-wave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 730 (and/or components thereof) generally will receive the signals, and the bus 705 then might carry the signals (and/or the data, instructions, etc. carried by the signals) to the working memory 735, from which the processor(s) 710 retrieves and executes the instructions. The instructions received by the working memory 735 may optionally be stored on a non-transitory storage device 725 either before or after execution by the processing unit 710.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

The methods, systems, devices, graphs, and tables discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or ±0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or ±0.1% from the specified value, as such variations are appropriate to in the context of the systems, devices, circuits, methods, and other implementations described herein. As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A dispensing unit, comprising:
a housing comprising a first end and a second end; and
a plurality of storage assemblies, wherein the plurality of storage assemblies are arranged in parallel with one another within the housing, each storage assembly comprising:
a plurality of compartments arranged linearly along an axis of the housing, each of the compartments being configured to store an item;
a cover coupled with the housing and extending between the first end and the second end such that the cover is positioned over the plurality of compartments;
a plurality of RF sensors that are configured to determine whether one or more of the plurality of compartments are empty, wherein each of the plurality of RF sensors is disposed in one of the plurality of compartments; and
an actuator coupled with the cover, the actuator being configured to retract the cover to draw a distal end of the cover from the first end toward the second end to expose a number of the plurality of compartments to expose a selected number of items stored in the plurality of compartments based on a reading from the plurality of RF sensors.

2. The dispensing unit of claim 1, wherein:
each of the plurality of compartments comprises a base and one or more walls; and
the base and the one or more walls comprise RF shielding.

3. The dispensing unit of claim 1, wherein:
the actuator comprises an encoder that determines how far the cover is retracted to expose the selected number of the plurality of compartments.

4. The dispensing unit of claim 1, wherein:
the plurality of RF sensors determine whether one or more of the plurality of compartments are empty based on whether an RF tag attached to an item is read within each of the one or more of the plurality of compartments.

5. The dispensing unit of claim 1, wherein:
the plurality of RF sensors are further configured to determine an inventory of a respective one of the plurality of storage assemblies.

6. A dispensing unit, comprising:
a housing comprising a first end and a second end;
a plurality of compartments arranged linearly along an axis of the housing, each of the compartments being configured to store an item;
a cover coupled with the housing and extending between the first end and the second end such that the cover is positioned over the plurality of compartments;
an actuator coupled with the cover;
at least one RF sensor;
one or more processors; and
a memory having instructions stored thereon that, when executed by the one or more processors, cause the one or more processors to:
determine whether one or more of the plurality of compartments are empty using the at least one RF sensor; and
cause the actuator to retract the cover to draw a leading edge of the cover from the first end toward the second end to expose a selected number of items stored in the plurality of compartments based on determining whether one or more of the plurality of compartments are empty; and
determine an inventory of the dispensing unit using the at least one RF sensor.

7. The dispensing unit of claim 6, wherein:
the dispensing unit is integrated into an electronically lockable drawer of a medication storage system.

8. The dispensing unit of claim 6, wherein:
the at least one RF sensor comprises an antenna that is disposed on a leading edge of the cover; and
the one or more processors determine whether one or more of the plurality of compartments are empty as the leading edge of the cover is moved along a length of the housing.

9. The dispensing unit of claim 6, wherein:
each of the plurality of compartments comprises a base and one or more walls; and
the base and the one or more walls comprise RF shielding.

10. The dispensing unit of claim 6, wherein:
the at least one RF sensor comprises a plurality of RF sensors; and
each of the plurality of RF sensors is disposed in one of the plurality of compartments.

11. The dispensing unit of claim 6, wherein:
the one or more processors determine whether one or more of the plurality of compartments are empty based on whether the at least one RF sensor reads an RF tag attached to an item within each of the one or more of the plurality of compartments.

12. A method of operating a dispensing mechanism, comprising:
receiving an input to dispense a selected number of items from a dispensing mechanism;
actuating a cover of the dispensing mechanism to retract a leading edge of the cover to expose a selected number of a plurality of compartments of the dispensing mechanism based on the selected number of items, wherein the plurality of compartments are arranged linearly along an axis of the dispensing mechanism, each of the compartments being configured to store an item; and
determining that at least one of the plurality of compartments is empty using at least one RF sensor of the dispensing mechanism, wherein:
the at least one RF sensor comprises an antenna that is disposed on a leading edge of the cover; and
determining that at least one of the plurality of compartments is empty comprises failing to read an RF tag of an item within the at least one of the plurality of compartments using the antenna as the leading edge of the cover is moved along the axis of the dispensing mechanism.

13. The method of operating a dispensing mechanism of claim 12, further comprising:
adjusting the selected number of the plurality of compartments to expose based on the determination that the at least one of the plurality of compartments is empty.

14. The method of operating a dispensing mechanism of claim 12, further comprising:
receiving an additional input to refill the plurality of compartments; and
actuating the cover of the dispensing mechanism to retract the leading edge of the cover to expose each of the plurality of compartments in response to the additional input.

15. The method of operating a dispensing mechanism of claim 12, wherein:
each of the plurality of compartments comprises a base and one or more walls; and the base and the one or more walls comprise RF shielding.

* * * * *